(12) United States Patent
Chau

(10) Patent No.: US 6,734,283 B1
(45) Date of Patent: May 11, 2004

(54) HUMAN PROTEINS RESPONSIBLE FOR NEDD8 ACTIVATION AND CONJUGATION

(75) Inventor: Vincent Chau, Brookline, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/216,430

(22) Filed: Dec. 18, 1998

Related U.S. Application Data

(60) Provisional application No. 60/096,525, filed on Aug. 12, 1998, and provisional application No. 60/068,209, filed on Dec. 19, 1997.

(51) Int. Cl.⁷ ............................................. C07K 1/00
(52) U.S. Cl. ........................... 530/350; 435/6; 435/7.1; 514/2; 536/23.1
(58) Field of Search ........................ 530/350; 536/23.1; 435/6, 7.1; 514/2

(56) References Cited

U.S. PATENT DOCUMENTS

| 5,932,442 A | 8/1999 | Lal et al. .................... 435/69.1 |
| 6,015,702 A | 1/2000 | Lal et al. .................... 435/193 |

FOREIGN PATENT DOCUMENTS

| WO | 99/15659 | 4/1999 |

OTHER PUBLICATIONS

Attwood et al. Which craft is best in bioinformatics? Comput. Chem. 2001, vol. 25(4), pp. 329–339.*
Ponting, C.P. Issues in predicting protein function from sequence. Brief. Bioinform. Mar. 2001, vol.2(1), pp. 19–29.*
Osaka et al.: A New NEDD8—Ligating System for Cullin–4A; (1998); *Genes & Development*; 12: pp. 2263–2268.
Hillier et al.: Homo Sapiens cDNA Clone Similar to Ubiquitin–Activating Enzyme; (1997); *EMEST Database Entry HS1201827, Accession No. AA402092, XP–002103406*, See Sequence.
Hillier et al.: Homo Sapiens cDNA Clone Similar to Ubiquitin–Activating Enzyme; (1997); *EMEST Database Entry HS1201636, Accession No. AA401865, XP–002103407*, See Sequence.
Hillier et al.: Homo Sapiens cDNA Clone Similar to Ubiquitin–Activating Enzyme; (1997); *EMEST Database Entry HS1201722, Accession No. AA401968, XP–002103408*, See Sequence.
National Cancer Institute, Cancer Genome Anatomy Project (CGAP): Homo Sapiens cDNA Clone Similar to Ubiquitin–Conjugating Enzyme E2; (1997); EMEST Database Entry HSAA61836, Accession No. AA261836, XP–002103409, See Sequence.
National Cancer Institute, Cancer Genome Anatomy Project (CGAP): Homo Sapiens cDNA Clone Similar to Ubiquitin–Conjugating Enzyme E2; (1997); EMEST Database Entry HSAA577116, Accession No. AA577116 XP–002103410, See Sequence.
Adams MD et al.: Homo Sapiens cDNA Clone Similar to Ubiquitin–Activating Enzyme; (1997); EMEST Database Entry HSZZ89371, Accession No. AA384235, XP–002103411, See Sequence.
Marra M et al.: Mus Musculus cDNA Clone Similar to Ubiquitin–Conjugating Enzyme E2; (1977); EMEST Database Entry AA671071, Accession No. AA671071, XP–002103412, See Sequence.
Kumar et al.: Cloning of cDNA Which Encodes a Novel Ubiquitin–Like Protein; (1993); *Biomedical and Biophysical Research Communications*; 195(1): pp. 393–399.
Kamitani, T., et al.: Characterization of NEDD8, a Developmentally Down–Regulated Ubiquitin–Like Protein; (1997); *J. Bio. Chem.* 272(45): pp. 28557–28562.
Marx, J.L.; Antibodies Made to Order; (1985); *Science*; 229: pp. 455–456.
Jones et al.; Replacing the Complementarity–Determining Regions in a Human Antibody with Those from a Mouse; (1986); *Nature*; 321: pp. 522–525.
Riechmann et al.; Reshaping Human Antibodies for Therapy; (1988); *Nature*; 332: pp. 323–327.
Verhoeyen et al.; Reshaping Human Antibodies: Grafting an Antilysozyme Activity; (1988); *Science*; 239: pp. 1534–1536.
Rodwell, J.D.; Engineering Monoclonal Antibodies; (1989); 342: pp. 99–100.
Clackson, T.P.; Genetically Engineered Monoclonal Antibodies; (1991); 30(S2): pp. 36–39.
Hershko et al.; The Ubiquitin System for Protein Degradation; (1992); *Annu. Rev. Biochem.*; 61: pp. 761–807.
Jentsch, S.; The Ubiquitin–Conjugation System; (1992); *Annu. Rev. Genet.* 26: pp. 179–207.
Seebach et al.; Structure and Reactivity of Five–and Six–Ring N,N–,N,O–, and O,O–Acetals: A Lesson in Allylic 1,3–Strain ($A_{1,3}$Strain ($A^{1,3}$Strain); (1992); *Helvetica Chimica Acta.*; 75:pp. 913–934.

(List continued on next page.)

Primary Examiner—Ponnathapu Achutamurthy
Assistant Examiner—Christian L Fronda
(74) Attorney, Agent, or Firm—Millennium Pharmaceuticals, Inc.

(57) ABSTRACT

The invention relates to covalent modification of proteins through their conjugation with other proteins. More particularly, the invention relates to the modulation of such conjugation involving the protein NEDD8. The invention provides compositions and methods for detecting and/or modulating the activation and/or conjugation of NEDD8, as well as compositions and methods for discovering molecules which are useful in detecting and/or modulating the activation and/or conjugation of NEDD8. The present invention arises from the purification and characterization of novel NEDD8 activating and conjugating enzymes.

8 Claims, 9 Drawing Sheets

OTHER PUBLICATIONS

Loeb et al; The Interferon–Inducible 15–kDa Ubiquitin Homolog Conjugates to Intracellular Proteins; (1992); *The Journal of Biological Chemistry*; 267(11): 7806–7813.

Kumar et al.; Identification of a Set of Genes with Developmentally Down–Regulated Expression in the Mouse Brain; (1992); *Biochem. and Biophys. Res. Communications*; 185(3): pp. 1155–1161.

Leyser et al.; Arabidopsis Auxin–Resistance Gene AXR1 Encodes a Protein Related to Ubiquitin–Activating Enzyme E1; (1993); 364: pp. 161–164.

Scheffner et al.; The HPV–16 E6 and E6–AP Complex Functions as a Ubiquitin–Protein Ligase in the Ubiquitination of p53; (1993); *Cell*; 75: pp. 495–505.

Gante, J.; Peptidomimetics—Tailored Enzyme Inhibitors; (1994); *Agnew Chem. Int. Ed. Engl.*; 33: pp. 1699–1720.

Rock et al.; Inhibitors of the Proteasome Block the Degradation of Most Cell Proteins and the Generation of Peptides Presented on MHC Class I Molecules; (1994); *Cell*; 78: pp. 761–771.

Thompson et al.; Clustal W: Improving the Sensitivity of Progessive Multiple Sequence Alignment Through Sequence Weighting, Position–Specific Gap . . . ; (1994); 22(22): pp. 4673–4680.

Liskamp, RMJ; Conformationally Restricted Amino Acids and Dipeptides, (non)Peptidomimetics and Secondary Structure Mimetics; (1994); *Recl. Trav. Chim. Pays–Bas*; 113: pp. 1–19.

Murray, A.; Cyclin Ubiquitination: The Destructive End of Mitosis; (1995); *Cell*: 81: pp. 149–152.

Horwell, D.C.; Use of the Chemical Structure of Peptides as the Starting Point to Design Nonpeptide Agonists and Antagonists at Peptide Receptors:; (1996); Bioorganic & Med. Chem. 4(10): pp. 1573–1576.

Okura et al.; Protection Against Fas/APO–1–and Tumor Necrosis Factor–Mediated Cell Death by a Novel Protein, Sentrin[1] ; (1996); *Jrnl of Immunology*; pp. 4277–4281.

Chow et al; APP–BP1, a Novel Protein that Binds to the Carboxyl–Terminal Region of the Amyloid Precursor Protein; (1996); *The Journal of Biological Chemistry*; 271(19): 11339–11346.

Townsley et al.; Dominant–Negative Cyclin–Selective Ubiquitin Carrier Protein E2–C/UbcH10 Blocks Cells in Metaphase; (1997); *Proc. Natl. Acad. Sci.*; 94: 2362–2367.

Hopkin, K.; Regulating Cellular Processes: the Power of Protein Degradation; (1997); *the Journal of NIH Research*; 9: pp. 36–42.

Kamitani et al.; Preferential Modification of Nuclear Proteins by a Novel Ubiquitin–Like Molecule; (1997); *The Journal of Biological Chemistry*; 272(22); pp. 14001–14004.

Altschul et al.; Gapped BLAST and PSI–BLAST: a New Generation of Protein Database Search Programs; (1997); *Nucleic Acids Research*; 25(17); pp. 3389–3402.

Kamitani et al.; Characterization of NEDD, a Developmentally Down–Regulated Ubiquitin–Like Protein; (1997); *The Journal of Biological Chemistry*; 272 (45): pp. 28557–28562.

* cited by examiner

| | |
|---|---|
| ATGGCTGTTGATGGTGGGTGTGGGGACACTGGAGACTGGGAAGGT<br> M  A  V  D  G  G  C  G  D  T  G  D  W  E  G | 45 |
| CGCTGGAACCATGTAAAGAAGTTCCTCGAGCGATCTGGACCCTTC<br> R  W  N  H  V  K  K  F  L  E  R  S  G  P  F | 90 |
| ACACACCCTGATTTCGAACCGAGCACTGAATCTCTCCAGTTCTTG<br> T  H  P  D  F  E  P  S  T  E  S  L  Q  F  L | 135 |
| TTAGATACATGTAAAGTTCTAGTCATTGGAGCTGGCGGCTTAGGA<br> L  D  T  C  K  V  L  V  I  G  A  G  G  L  G | 180 |
| TGTGAGCTCCTGAAAAATCTGGCCTTGTCTGGTTTTAGACAGATT<br> C  E  L  L  K  N  L  A  L  S  G  F  R  Q  I | 225 |
| CATGTTATAGATATGGACACTATAGATGTTTCCAATCTAAATAGG<br> H  V  I  D  M  D  T  I  D  V  S  N  L  N  R | 270 |
| CAGTTTTTATTTAGGCCTAAAGATATTGGAAGACCTAAGGCTGAA<br> Q  F  L  F  R  P  K  D  I  G  R  P  K  A  E | 315 |
| GTTGCTGCAGAATTTCTAAATGACAGAGTTCCTAATTGCAATGTA<br> V  A  A  E  F  L  N  D  R  V  P  N  C  N  V | 360 |
| GTTCCACATTTCAACAAGATTCAAGATTTTAACGACACTTTCTAT<br> V  P  H  F  N  K  I  Q  D  F  N  D  T  F  Y | 405 |
| CGACAATTTCATATTATTGTATGTGGACTGGACTCTATCATCGCC<br> R  Q  F  H  I  I  V  C  G  L  D  S  I  I  A | 450 |
| AGAAGATGGATAAATGGCATGCTGATATCTCTTCTAAATTATGAA<br> R  R  W  I  N  G  M  L  I  S  L  L  N  Y  E | 495 |
| GATGGTGTCTTAGATCCAAGCTCCATTGTCCCTTTGATAGATGGG<br> D  G  V  L  D  P  S  S  I  V  P  L  I  D  G | 540 |
| GGGACAGAAGGTTTTAAAGGAAATGCCCGGGTGATTCTGCCTGGA<br> G  T  E  G  F  K  G  N  A  R  V  I  L  P  G | 585 |
| ATGACTGCTTGTATCGAATGCACGCTGGAACTTTATCCACCACAG<br> M  T  A  C  I  E  C  T  L  E  L  Y  P  P  Q | 630 |
| GTTAATTTTCCATGTGCACCATTGCATCTATGCCCAGGCTACCA<br> V  N  F  P  M  (C\*)T  I  A  S  M  P  R  L  P | 675 |
| GAACACTGTATTGAGTATGTAAGGATGTTGCAGTGGCCTAAGGAG<br> E  H  C  I  E  Y  V  R  M  L  Q  W  P  K  <u>E</u> | 720 |
| CAGCCTTTTGGAGAAGGGGTTCCATTAGATAGAGATGATCCTGAA<br> <u>Q  P  F  G  E  G  V  P  L  D  G  D  D  P  E</u> | 765 |
| CATATACAATGGATTTTCCAAAAATCCCTAGAGAGAGCATCACAA<br> <u>H  I  Q  W  I  F  Q  K  S  L  E  R  A  S  Q</u> | 810 |
| TATAATATTAGGGGTGTTACGTATAGGCTCACTCAAGGGGTAGTA<br> Y  N  I  R  G  V  T  Y  R  L  T  Q  G  V  V | 855 |
| AAAAGAATCATTCCTGCAGTAGCTTCCACAAATGCAGTCATTGCA<br> K  R  I  I  P  A  V  A  S  T  N  A  V  I  A | 900 |
| GCTGTGTGTGCCACTGAGGTTTTTAAAATAGCCACAAGTGCATAC<br> A  V  C  A  T  E  V  F  K  I  A  T  S  A  Y | 945 |
| ATTCCCTTGAATAATTACTTGGTGTTTAATGATGTAGATGGGCTG<br> I  P  L  N  N  Y  L  C  F  N  D  V  D  G  L | 990 |
| TATACATACACATTTGAAGCAGAAAGAAAGGAAAACTGCCCAGCT<br> Y  T  Y  T  F  E  A  E  R  K  E  N  C  P  A | 1035 |
| TGTAGCCAGCTTCCTCAAAATATTCAGTTTTCTCCATCAGCTAAA<br> C  S  Q  L  P  Q  N  I  Q  F  S  P  S  A  K | 1080 |
| CTACAGGAGGTTTTGGATTATCTAACCAATAGTGCTTCTCTGCAA<br> L  Q  E  V  L  D  Y  L  T  N  S  A  S  L  Q | 1125 |
| ATGAAATCTCCAGCCATCACAGCCACCCTAGAGGGAAAAAATAGA<br> M  K  <u>S  P  A  I  T  A  T  L  E  G  K</u>  N  R | 1170 |
| ACACTTTACTTACAGTCGGTAACCTCTATTGAAGAACGAACAAGG<br> T  L  Y  L  Q  S  V  T  S  I  E  E  R  T  R | 1215 |
| CCAAATCTCTCCAAAACATTGAAAGAATTGGGGCTTGTTGATGGA<br> P  N  L  S  K  T  L  K  E  L  G  L  V  D  G | 1260 |
| CAAGAACTGGCGGTTGCTGATGTCACCACCCCACAGACTGTACTA<br> Q  E  L  A  V  A  D  V  T  T  P  Q  T  V  L | 1305 |
| TTCAAACTTCATTTTACTTCTTAA    1329<br> F  K  L  H  F  T  S | |

FIG. 1

```
+1    M  I  K  L     F  S  L     K  Q  Q     K  K  E  E     E  S  A
1     ATGATCAAGC TGTTCTCGCT GAAGCAGCAG AAGAAGGAGG AGGAGTCGGC
      TACTAGTTCG ACAAGAGCGA CTTCGTCGTC TTCTTCCTCC TCCTCAGCCG
```
```
+1    G  G  T     K  G  S  S     K  K  A     S  A  A     Q  L  R
51    GGGCGGCACC AAGGGCAGCA GCAAGAAGGC GTCGGCGGCG CAGCTGCGGA
      CCCGCCGTGG TTCCCGTCGT CGTTCTTCCG CAGCCGCCGC GTCGACGCCT
```
```
+1    I  Q  K  D     I  N  E     L  N  L  P     K  T  C     D  I  S
101   TCCAGAAGGA CATAAACGAG CTGAACCTGC CAAGACGTG TGATATCAGC
      AGGTCTTCCT GTATTTGCTC GACTTGGACG GGTTCTGCAC ACTATAGTCG
```
```
+1    F  S  D  P     D  D  L     L  N  F     K  L  V     C  P  D
151   TTCTCAGATC CAGACGACCT CCTCAACTTC AAGCTGGTCA TCTGTCCTGA
      AAGAGTCTAG GTCTGCTGGA GGAGTTGAAG TTCGACCAGT AGACAGGACT
```
```
+1    E  G  F     Y  K  S     G    K  F  V     F  S  F     K  V  G
201   TGAGGGCTTC TACAAGAGTG GAAGTTTGT GTTCAGTTTT AAGGTGGGCC
      ACTCCCGAAG ATGTTCTCAC CCTTCAAACA CAAGTCAAAA TTCCACCCGG
```
```
+1    Q  G  Y  P     H  D  P     P  K  V  K     C  E  T     M  V  Y
251   AGGGTTACCC GCATGATCCC CCCAAGGTGA AGTGTGAGAC AATGGTCTAT
      TCCCAATGGG CGTACTAGGG GGGTTCCACT TCACACTCTG TTACCAGATA
```
```
+1    H  P  N     I  D  L  E     G  N  V     ⒞  L  N  I     L  R  E
301   CACCCCAACA TTGACCTCGA GGGCAACGTC TGCCTCAACA TCCTCAGAGA
      GTGGGGTTGT AACTGGAGCT CCCGTTGCAG ACGGAGTTGT AGGAGTCTCT
```
```
+1    D  W  K     P  V  L  T     I  N  S     I  I  Y     G  L  Q
351   GGACTGGAAG CCAGTCCTTA CGATAAACTC ATAATTTAT GGCCTGCAGT
      CCTGACCTTC GGTCAGGAAT GCTATTTGAG GTATTAAATA CCGGACGTCA
```
```
+1    Y  L  F  L     E  P  N     P  E  D  P     L  N  K     E  A  A
401   ATCTCTTCTT GGAGCCCAAC CCCGAGGACC CACTGAACAA GGAGGCCGCA
      TAGAGAAGAA CCTCGGGTTG GGGCTCCTGG GTGACTTGTT CCTCCGGCGT
```
```
+1    E  V  L  Q     N  N  R     R  L  F     E  Q  N  V     Q  R  S
451   GAGGTCCTGC AGAACAACCG GCGGCTGTTT GAGCAGAACG TGCAGCGCTC
      CTCCAGGACG TCTTGTTGGC CGCCGACAAA CTCGTCTTGC ACGTCGCGAG
```
```
+1    M  R  G     G  Y  I  G     S  T  Y     F  E  R     C  L  K
501   CATGCGGGGT GGCTACATCG GCTCCACCTA CTTTGAGCGC TGCCTGAAAT
      GTACGCCCCA CCGATGTAGC CGAGGTGGAT GAAACTCGCG ACGGACTTTA
```
```
+1    *
551   AG
      TC
```

FIG. 2

```
              *        20           *        40           *        60           *        80
yUbc12 : MLKIRQFQK.KKQKENENSS..SIQPNILSAARIRLKRDLDSIDLPFTVTLNVITSPDSADRSQSPKLEVIVRPDEGMYNYGSINFN: 83
NCE1   : MIKIFSLKQQKEEESAGGTKGSSKKASAAQIRIQKDINEINLPKTCDISFSD.ED...LINFKLVICPDEGFYKSGKFVES: 79

*       100           *       120           *       140           *       160
yUbc12 : LDFNEVIPLEPPKVMQLKKIFHPNIDIKGNVCLNILREDWSPAFDLQSIIIGILFLFLEPNPDPLNKDAAKIICEGEKEFAEAV: 168
NCE1   : FKVGQGYHDPPKVKCETMVYHPNIDLFGNVCLNIIFGNVMLTINSIIYGLQYLFLEPNPEDPLNKEAAFVLQNNRRLFEQNV: 164

*       180
yUbc12 : RLIMSGGSIEHVKYDNIVSP:188
NCE1   : QRSMRGGMIGSTYFERCLK. :183
```

FIG. 3

```
+1    M   L   T   L   A   S   K   L   K   R   D   D   G   L   K   G   S
1     ATGCTAACGC TAGCAAGTAA ACTGAAGCGT GACGATGGTC TCAAAGGGTC
      TACGATTGCG ATCGTTCATT TGACTTCGCA CTGCTACCAG AGTTTCCCAG
-----------------------------------------------------------------------
+1    R   T   A   A   T   A   S   D   S   T   R   R   V   S   V   R
51    CCGGACGGCA GCCACAGCGT CCGACTCGAC TCGGAGGGTT TCTGTGAGAG
      GGCCTGCCGT CGGTGTCGCA GGCTGAGCTG AGCCTCCCAA AGACACTCTC
-----------------------------------------------------------------------
+1    D   K   L   L   V   K   E   V   A   E   L   E   A   N   L   P   C
101   ACAAATTGCT TGTTAAAGAG GTTGCAGAAC TTGAAGCTAA TTTACCTTGT
      TGTTTAACGA ACAATTTCTC CAACGTCTTG AACTTCGATT AAATGGAACA
-----------------------------------------------------------------------
+1    T   C   K   V   H   F   P   D   P   N   K   L   B   C   F   Q   L
                                              HindIII
                                              ~~~~~~
151   ACATGTAAAG TGCATTTTCC TGATCCAAAC AAGCTTCATT GTTTTCAGCT
      TGTACATTTC ACGTAAAAGG ACTAGGTTTG TTCGAAGTAA CAAAAGTCGA
-----------------------------------------------------------------------
+1    T   V   T   P   D   E   G   Y   Y   Q   G   G   K   F   Q   F
201   AACAGTAACC CCAGATGAGG GTTACTACCA GGGTGGAAAA TTTCAGTTTG
      TTGTCATTGG GGTCTACTCC CAATGATGGT CCCACCTTTT AAAGTCAAAC
-----------------------------------------------------------------------
+1    E   T   E   V   P   D   A   Y   N   M   V   P   P   K   V   K   C
251   AAACTGAAGT TCCCGATGCG TACAACATGG TGCCTCCCAA AGTGAAATGC
      TTTGACTTCA AGGGCTACGC ATGTTGTACC ACGGAGGGTT TCACTTTACG
-----------------------------------------------------------------------
+1    L   T   K   I   W   H   P   N   I   T   E   T   G   E   I   [C] L
301   CTGACCAAGA TCTGGCACCC CAACATCACA GAGACAGGGG AAATATGTCT
      GACTGGTTCT AGACCGTGGG GTTGTAGTGT CTCTGTCCCC TTTATACAGA
-----------------------------------------------------------------------
+1    S   L   L   R   E   H   S   I   D   G   T   G   W   A   P   T
351   GAGTTTATTG AGAGAACATT CAATTGATGG CACTGGCTGG GCTCCCACAA
      CTCAAATAAC TCTCTTGTAA GTTAACTACC GTGACCGACC CGAGGGTGTT
-----------------------------------------------------------------------
+1    R   T   L   K   D   V   V   W   G   L   N   S   L   F   T   D   L
401   GAACATTAAA GGATGTCGTT TGGGGATTAA ACTCTTTGTT TACTGATCTT
      CTTGTAATTT CCTACAGCAA ACCCCTAATT TGAGAAACAA ATGACTAGAA
-----------------------------------------------------------------------
+1    L   N   F   D   D   P   L   N   I   E   A   A   E   H   H   L   R
                                              PstI
                                              ~~~~~~
451   TTGAATTTTG ATGATCCACT GAATATTGAA GCTGCAGAAC ATCATTTGCG
      AACTTAAAAC TACTAGGTGA CTTATAACTT CGACGTCTTG TAGTAAACGC
-----------------------------------------------------------------------
+1    D   K   E   D   F   R   N   K   V   D   D   Y   I   K   R   Y
501   GGACAAGGAG GACTTCCGGA ATAAAGTGGA TGACTACATC AAACGTTATG
      CCTGTTCCTC CTGAAGGCCT TATTTCACCT ACTGATGTAG TTTGCAATAC
-----------------------------------------------------------------------
+1    A   R   *
551   CCAGATGA
      GGTCTACT
-----------------------------------------------------------------------
```

FIG. 5

```
Hsubc17   : MLTLASKLKRDDGLKGSRTAATASDSTRRVSVRDKLIVKEVAELEPANLPCTCK....VHFPDPNKLFCEQLTVTPDEGMYQGG :  79
Ce275850  : MFNLQKRINGNN.EDG.......RYLETRIAVRDKLIAQEIQQLETTALRDQKQLWHLEVPSTSCLHELELTVTPQEGHYRGG :  75

*              *              *              *              *              *
Hsubc17   : KFQFETEVEPDAYNMVPEKVKCLITKIWHPNITETGEICLSILREHSIDGTGWAPTRTILKDVVMGINSLFIDLNPDDPLNIEAA : 162
Ce275850  : KFRFKITVPPENNVEPVVKCLITKMWHPNINEDGSICLSILRQNSIDQYGWRPTRNLTDVVHGIVSLFNDIMDFNDALNIQAA : 158

*              *
Hsubc17   : EHHLRDKEDERNKVDDYIKRYAR : 185
Ce275850  : QMWSWNRESENHRVREYISRYC. : 180
```

```
            340         *         360         *
NCE1     : ............................................. :  -
NCE2     : ............................................. :  -
UBC1     : ............................................. :  -
UBC2b    : ............................................. :  -
UBC2a    : ............................................. :  -
Cdc34a   : ............................................. :  -
UB5B     : ............................................. :  -
UB5C     : ............................................. :  -
UB5A     : ............................................. :  -
UbcH6    : ............................................. :  -
UbcH7    : ............................................. :  -
UbcH8    : ............................................. :  -
UBE2G    : ............................................. :  -
UBCH(8)  : ............................................. :  -
UBC9     : ............................................. :  -
UBCH10   : ............................................. :  -
UBC13    : ............................................. :  -
```

LANE 1: NO NCE
LANE 2: + NCE1
LANE 3: + NCE2; ARROW INDICATES Nedd8 THIOESTER OF NCE2
LANE 4: SAME AS LANE 2 BUT + DTT
LANE 5: SAME AS LANE 2 BUT + DTT

SEQUENCE LISTING

```
<160> NUMBER OF SEQ ID NOS: 38

<210> SEQ ID NO 1
<211> LENGTH: 1329
<212> TYPE: DNA
<213> ORGANISM: Human
<220> FEATURE:
<221> NAME/KEY: misc_feature
<222> LOCATION: (1)..(1329)
<223> OTHER INFORMATION: NAE1-beta
<221> NAME/KEY: CDS
<222> LOCATION: (1)..(1329)
<223> OTHER INFORMATION:

<400> SEQUENCE: 1 atg gct gtt gat ggt ggg tgt ggg gac act gga gac tgg gaa ggt cgc      48
Met Ala Val Asp Gly Gly Cys Gly Asp Thr Gly Asp Trp Glu Gly Arg
1               5                   10                  15 tgg aac cat gta aag aag ttc ctc gag cga tct gga ccc ttc aca cac      96
Trp Asn His Val Lys Lys Phe Leu Glu Arg Ser Gly Pro Phe Thr His
                20                  25                  30 cct gat ttc gaa ccg agc act gaa tct ctc cag ttc ttg tta gat aca     144
Pro Asp Phe Glu Pro Ser Thr Glu Ser Leu Gln Phe Leu Leu Asp Thr
            35                  40                  45 tgt aaa gtt cta gtc att gga gct ggc ggc tta gga tgt gag ctc ctg     192
Cys Lys Val Leu Val Ile Gly Ala Gly Gly Leu Gly Cys Glu Leu Leu
        50                  55                  60 aaa aat ctg gcc ttg tct ggt ttt aga cag att cat gtt ata gat atg     240
Lys Asn Leu Ala Leu Ser Gly Phe Arg Gln Ile His Val Ile Asp Met
65                  70                  75                  80 gac act ata gat gtt tcc aat cta aat agg cag ttt tta ttt agg cct     288
Asp Thr Ile Asp Val Ser Asn Leu Asn Arg Gln Phe Leu Phe Arg Pro
                85                  90                  95 aaa gat att gga aga cct aag gct gaa gtt gct gca gaa ttt cta aat     336
Lys Asp Ile Gly Arg Pro Lys Ala Glu Val Ala Ala Glu Phe Leu Asn
            100                 105                 110 gac aga gtt cct aat tgc aat gta gtt cca cat ttc aac aag att caa     384
Asp Arg Val Pro Asn Cys Asn Val Val Pro His Phe Asn Lys Ile Gln
        115                 120                 125 gat ttt aac gac act ttc tat cga caa ttt cat att att gta tgt gga     432
Asp Phe Asn Asp Thr Phe Tyr Arg Gln Phe His Ile Ile Val Cys Gly
```

```
            130                 135                 140
ctg gac tct atc atc gcc aga aga tgg ata aat ggc atg ctg ata tct      480
Leu Asp Ser Ile Ile Ala Arg Arg Trp Ile Asn Gly Met Leu Ile Ser
145                 150                 155                 160 ctt cta aat tat gaa gat ggt gtc tta gat cca agc tcc att gtc cct      528
Leu Leu Asn Tyr Glu Asp Gly Val Leu Asp Pro Ser Ser Ile Val Pro
                165                 170                 175 ttg ata gat ggg ggg aca gaa ggt ttt aaa gga aat gcc cgg gtg att      576
Leu Ile Asp Gly Gly Thr Glu Gly Phe Lys Gly Asn Ala Arg Val Ile
            180                 185                 190 ctg cct gga atg act gct tgt atc gaa tgc acg ctg gaa ctt tat cca      624
Leu Pro Gly Met Thr Ala Cys Ile Glu Cys Thr Leu Glu Leu Tyr Pro
        195                 200                 205 cca cag gtt aat ttt ccc atg tgc acc att gca tct atg ccc agg cta      672
Pro Gln Val Asn Phe Pro Met Cys Thr Ile Ala Ser Met Pro Arg Leu
    210                 215                 220 cca gaa cac tgt att gag tat gta agg atg ttg cag tgg cct aag gag      720
Pro Glu His Cys Ile Glu Tyr Val Arg Met Leu Gln Trp Pro Lys Glu
225                 230                 235                 240 cag cct ttt gga gaa ggg gtt cca tta gat aga gat gat cct gaa cat      768
Gln Pro Phe Gly Glu Gly Val Pro Leu Asp Arg Asp Asp Pro Glu His
                245                 250                 255 ata caa tgg att ttc caa aaa tcc cta gag aga gca tca caa tat aat      816
Ile Gln Trp Ile Phe Gln Lys Ser Leu Glu Arg Ala Ser Gln Tyr Asn
            260                 265                 270 att agg ggt gtt acg tat agg ctc act caa ggg gta gta aaa aga atc      864
Ile Arg Gly Val Thr Tyr Arg Leu Thr Gln Gly Val Val Lys Arg Ile
        275                 280                 285 att cct gca gta gct tcc aca aat gca gtc att gca gct gtg tgt gcc      912
Ile Pro Ala Val Ala Ser Thr Asn Ala Val Ile Ala Ala Val Cys Ala
    290                 295                 300 act gag gtt ttt aaa ata gcc aca agt gca tac att ccc ttg aat aat      960
Thr Glu Val Phe Lys Ile Ala Thr Ser Ala Tyr Ile Pro Leu Asn Asn
305                 310                 315                 320 tac ttg gtg ttt aat gat gta gat ggg ctg tat aca tac aca ttt gaa     1008
Tyr Leu Val Phe Asn Asp Val Asp Gly Leu Tyr Thr Tyr Thr Phe Glu
                325                 330                 335 gca gaa aga aag gaa aac tgc cca gct tgt agc cag ctt cct caa aat     1056
Ala Glu Arg Lys Glu Asn Cys Pro Ala Cys Ser Gln Leu Pro Gln Asn
            340                 345                 350 att cag ttt tct cca tca gct aaa cta cag gag gtt ttg gat tat cta     1104
Ile Gln Phe Ser Pro Ser Ala Lys Leu Gln Glu Val Leu Asp Tyr Leu
        355                 360                 365 acc aat agt gct tct ctg caa atg aaa tct cca gcc atc aca gcc acc     1152
Thr Asn Ser Ala Ser Leu Gln Met Lys Ser Pro Ala Ile Thr Ala Thr
    370                 375                 380 cta gag gga aaa aat aga aca ctt tac tta cag tcg gta acc tct att     1200
Leu Glu Gly Lys Asn Arg Thr Leu Tyr Leu Gln Ser Val Thr Ser Ile
385                 390                 395                 400 gaa gaa cga aca agg cca aat ctc tcc aaa aca ttg aaa gaa ttg ggg     1248
Glu Glu Arg Thr Arg Pro Asn Leu Ser Lys Thr Leu Lys Glu Leu Gly
                405                 410                 415 ctt gtt gat gga caa gaa ctg gcg gtt gct gat gtc acc acc cca cag     1296
Leu Val Asp Gly Gln Glu Leu Ala Val Ala Asp Val Thr Thr Pro Gln
            420                 425                 430 act gta cta ttc aaa ctt cat ttt act tct taa                         1329
Thr Val Leu Phe Lys Leu His Phe Thr Ser
        435                 440
```

```
<210> SEQ ID NO 2
<211> LENGTH: 442
<212> TYPE: PRT
<213> ORGANISM: Human
<220> FEATURE:
<221> NAME/KEY: misc_feature
<222> LOCATION: (1)..(1329)
<223> OTHER INFORMATION: NAE1-beta

<400> SEQUENCE: 2
```

Met Ala Val Asp Gly Gly Cys Gly Asp Thr Gly Asp Trp Glu Gly Arg
1               5                   10                  15

Trp Asn His Val Lys Lys Phe Leu Glu Arg Ser Gly Pro Phe Thr His
            20                  25                  30

Pro Asp Phe Glu Pro Ser Thr Glu Ser Leu Gln Phe Leu Leu Asp Thr
        35                  40                  45

Cys Lys Val Leu Val Ile Gly Ala Gly Gly Leu Gly Cys Glu Leu Leu
    50                  55                  60

Lys Asn Leu Ala Leu Ser Gly Phe Arg Gln Ile His Val Ile Asp Met
65                  70                  75                  80

Asp Thr Ile Asp Val Ser Asn Leu Asn Arg Gln Phe Leu Phe Arg Pro
                85                  90                  95

Lys Asp Ile Gly Arg Pro Lys Ala Glu Val Ala Ala Glu Phe Leu Asn
            100                 105                 110

Asp Arg Val Pro Asn Cys Asn Val Val Pro His Phe Asn Lys Ile Gln
        115                 120                 125

Asp Phe Asn Asp Thr Phe Tyr Arg Gln Phe His Ile Ile Val Cys Gly
    130                 135                 140

Leu Asp Ser Ile Ile Ala Arg Arg Trp Ile Asn Gly Met Leu Ile Ser
145                 150                 155                 160

Leu Leu Asn Tyr Glu Asp Gly Val Leu Asp Pro Ser Ser Ile Val Pro
                165                 170                 175

Leu Ile Asp Gly Gly Thr Glu Gly Phe Lys Gly Asn Ala Arg Val Ile
            180                 185                 190

Leu Pro Gly Met Thr Ala Cys Ile Glu Cys Thr Leu Glu Leu Tyr Pro
        195                 200                 205

Pro Gln Val Asn Phe Pro Met Cys Thr Ile Ala Ser Met Pro Arg Leu
    210                 215                 220

Pro Glu His Cys Ile Glu Tyr Val Arg Met Leu Gln Trp Pro Lys Glu
225                 230                 235                 240

Gln Pro Phe Gly Glu Gly Val Pro Leu Asp Arg Asp Pro Glu His
                245                 250                 255

Ile Gln Trp Ile Phe Gln Lys Ser Leu Glu Arg Ala Ser Gln Tyr Asn
            260                 265                 270

Ile Arg Gly Val Thr Tyr Arg Leu Thr Gln Gly Val Val Lys Arg Ile
        275                 280                 285

Ile Pro Ala Val Ala Ser Thr Asn Ala Val Ile Ala Ala Val Cys Ala
    290                 295                 300

Thr Glu Val Phe Lys Ile Ala Thr Ser Ala Tyr Ile Pro Leu Asn Asn
305                 310                 315                 320

Tyr Leu Val Phe Asn Asp Val Asp Gly Leu Tyr Thr Tyr Thr Phe Glu
                325                 330                 335

Ala Glu Arg Lys Glu Asn Cys Pro Ala Cys Ser Gln Leu Pro Gln Asn
            340                 345                 350

Ile Gln Phe Ser Pro Ser Ala Lys Leu Gln Glu Val Leu Asp Tyr Leu
        355                 360                 365

```
Thr Asn Ser Ala Ser Leu Gln Met Lys Ser Pro Ala Ile Thr Ala Thr
        370                 375                 380

Leu Glu Gly Lys Asn Arg Thr Leu Tyr Leu Gln Ser Val Thr Ser Ile
385                 390                 395                 400

Glu Glu Arg Thr Arg Pro Asn Leu Ser Lys Thr Leu Lys Glu Leu Gly
                405                 410                 415

Leu Val Asp Gly Gln Glu Leu Ala Val Ala Asp Val Thr Thr Pro Gln
                420                 425                 430

Thr Val Leu Phe Lys Leu His Phe Thr Ser
        435                 440
```

<210> SEQ ID NO 3
<211> LENGTH: 552
<212> TYPE: DNA
<213> ORGANISM: Human
<220> FEATURE:
<221> NAME/KEY: misc_feature
<222> LOCATION: (1)..(552)
<223> OTHER INFORMATION: NEDD8-conjugating enzyme 1 (NCE1)
<221> NAME/KEY: CDS
<222> LOCATION: (1)..(552)
<223> OTHER INFORMATION:

<400> SEQUENCE: 3

```
atg atc aag ctg ttc tcg ctg aag cag cag aag aag gag gag gag tcg     48
Met Ile Lys Leu Phe Ser Leu Lys Gln Gln Lys Lys Glu Glu Glu Ser
1               5                   10                  15 gcg ggc ggc acc aag ggc agc agc aag aag gcg tcg gcg gcg cag ctg     96
Ala Gly Gly Thr Lys Gly Ser Ser Lys Lys Ala Ser Ala Ala Gln Leu
                20                  25                  30 cgg atc cag aag gac ata aac gag ctg aac ctg ccc aag acg tgt gat    144
Arg Ile Gln Lys Asp Ile Asn Glu Leu Asn Leu Pro Lys Thr Cys Asp
            35                  40                  45 atc agc ttc tca gat cca gac gac ctc ctc aac ttc aag ctg gtc atc    192
Ile Ser Phe Ser Asp Pro Asp Asp Leu Leu Asn Phe Lys Leu Val Ile
        50                  55                  60 tgt cct gat gag ggc ttc tac aag agt ggg aag ttt gtg ttc agt ttt    240
Cys Pro Asp Glu Gly Phe Tyr Lys Ser Gly Lys Phe Val Phe Ser Phe
65                  70                  75                  80 aag gtg ggc cag ggt tac ccg cat gat ccc ccc aag gtg aag tgt gag    288
Lys Val Gly Gln Gly Tyr Pro His Asp Pro Pro Lys Val Lys Cys Glu
                85                  90                  95 aca atg gtc tat cac ccc aac att gac ctc gag ggc aac gtc tgc ctc    336
Thr Met Val Tyr His Pro Asn Ile Asp Leu Glu Gly Asn Val Cys Leu
            100                 105                 110 aac atc ctc aga gag gac tgg aag cca gtc ctt acg ata aac tcc ata    384
Asn Ile Leu Arg Glu Asp Trp Lys Pro Val Leu Thr Ile Asn Ser Ile
        115                 120                 125 att tat ggc ctg cag tat ctc ttc ttg gag ccc aac ccc gag gac cca    432
Ile Tyr Gly Leu Gln Tyr Leu Phe Leu Glu Pro Asn Pro Glu Asp Pro
130                 135                 140 ctg aac aag gag gcc gca gag gtc ctg cag aac aac cgg cgg ctg ttt    480
Leu Asn Lys Glu Ala Ala Glu Val Leu Gln Asn Asn Arg Arg Leu Phe
145                 150                 155                 160 gag cag aac gtg cag cgc tcc atg cgg ggt ggc tac atc ggc tcc acc    528
Glu Gln Asn Val Gln Arg Ser Met Arg Gly Gly Tyr Ile Gly Ser Thr
                165                 170                 175 tac ttt gag cgc tgc ctg aaa tag                                    552
Tyr Phe Glu Arg Cys Leu Lys
                180
```

```
<210> SEQ ID NO 4
<211> LENGTH: 183
<212> TYPE: PRT
<213> ORGANISM: Human
<220> FEATURE:
<221> NAME/KEY: misc_feature
<222> LOCATION: (1)..(552)
<223> OTHER INFORMATION: NEDD8-conjugating enzyme 1 (NCE1)

<400> SEQUENCE: 4

Met Ile Lys Leu Phe Ser Leu Lys Gln Gln Lys Lys Glu Glu Glu Ser
1               5                   10                  15

Ala Gly Gly Thr Lys Gly Ser Ser Lys Lys Ala Ser Ala Ala Gln Leu
            20                  25                  30

Arg Ile Gln Lys Asp Ile Asn Glu Leu Asn Leu Pro Lys Thr Cys Asp
        35                  40                  45

Ile Ser Phe Ser Asp Pro Asp Asp Leu Leu Asn Phe Lys Leu Val Ile
    50                  55                  60

Cys Pro Asp Glu Gly Phe Tyr Lys Ser Gly Lys Phe Val Phe Ser Phe
65                  70                  75                  80

Lys Val Gly Gln Gly Tyr Pro His Asp Pro Pro Lys Val Lys Cys Glu
                85                  90                  95

Thr Met Val Tyr His Pro Asn Ile Asp Leu Glu Gly Asn Val Cys Leu
            100                 105                 110

Asn Ile Leu Arg Glu Asp Trp Lys Pro Val Leu Thr Ile Asn Ser Ile
        115                 120                 125

Ile Tyr Gly Leu Gln Tyr Leu Phe Leu Glu Pro Asn Pro Glu Asp Pro
    130                 135                 140

Leu Asn Lys Glu Ala Ala Glu Val Leu Gln Asn Asn Arg Arg Leu Phe
145                 150                 155                 160

Glu Gln Asn Val Gln Arg Ser Met Arg Gly Gly Tyr Ile Gly Ser Thr
                165                 170                 175

Tyr Phe Glu Arg Cys Leu Lys
            180

<210> SEQ ID NO 5
<211> LENGTH: 558
<212> TYPE: DNA
<213> ORGANISM: Human
<220> FEATURE:
<221> NAME/KEY: misc_feature
<222> LOCATION: (1)..(558)
<223> OTHER INFORMATION: NEDD8-conjugating enzyme 2 (NCE2)
<221> NAME/KEY: CDS
<222> LOCATION: (1)..(558)
<223> OTHER INFORMATION:

<400> SEQUENCE: 5 atg cta acg cta gca agt aaa ctg aag cgt gac gat ggt ctc aaa ggg    48
Met Leu Thr Leu Ala Ser Lys Leu Lys Arg Asp Asp Gly Leu Lys Gly
1               5                   10                  15 tcc cgg acg gca gcc aca gcg tcc gac tcg act cgg agg gtt tct gtg    96
Ser Arg Thr Ala Ala Thr Ala Ser Asp Ser Thr Arg Arg Val Ser Val
            20                  25                  30 aga gac aaa ttg ctt gtt aaa gag gtt gca gaa ctt gaa gct aat tta   144
Arg Asp Lys Leu Leu Val Lys Glu Val Ala Glu Leu Glu Ala Asn Leu
        35                  40                  45 cct tgt aca tgt aaa gtg cat ttt cct gat cca aac aag ctt cat tgt   192
Pro Cys Thr Cys Lys Val His Phe Pro Asp Pro Asn Lys Leu His Cys
    50                  55                  60
```

```
ttt cag cta aca gta acc cca gat gag ggt tac tac cag ggt gga aaa      240
Phe Gln Leu Thr Val Thr Pro Asp Glu Gly Tyr Tyr Gln Gly Gly Lys
 65                  70                  75                  80 ttt cag ttt gaa act gaa gtt ccc gat gcg tac aac atg gtg cct ccc      288
Phe Gln Phe Glu Thr Glu Val Pro Asp Ala Tyr Asn Met Val Pro Pro
                 85                  90                  95 aaa gtg aaa tgc ctg acc aag atc tgg cac ccc aac atc aca gag aca      336
Lys Val Lys Cys Leu Thr Lys Ile Trp His Pro Asn Ile Thr Glu Thr
            100                 105                 110 ggg gaa ata tgt ctg agt tta ttg aga gaa cat tca att gat ggc act      384
Gly Glu Ile Cys Leu Ser Leu Leu Arg Glu His Ser Ile Asp Gly Thr
        115                 120                 125 ggc tgg gct ccc aca aga aca tta aag gat gtc gtt tgg gga tta aac      432
Gly Trp Ala Pro Thr Arg Thr Leu Lys Asp Val Val Trp Gly Leu Asn
    130                 135                 140 tct ttg ttt act gat ctt ttg aat ttt gat gat cca ctg aat att gaa      480
Ser Leu Phe Thr Asp Leu Leu Asn Phe Asp Asp Pro Leu Asn Ile Glu
145                 150                 155                 160 gct gca gaa cat cat ttg cgg gac aag gag gac ttc cgg aat aaa gtg      528
Ala Ala Glu His His Leu Arg Asp Lys Glu Asp Phe Arg Asn Lys Val
                165                 170                 175 gat gac tac atc aaa cgt tat gcc aga tga                              558
Asp Asp Tyr Ile Lys Arg Tyr Ala Arg
            180                 185

<210> SEQ ID NO 6
<211> LENGTH: 185
<212> TYPE: PRT
<213> ORGANISM: Human
<220> FEATURE:
<221> NAME/KEY: misc_feature
<222> LOCATION: (1)..(558)
<223> OTHER INFORMATION: NEDD8-conjugating enzyme 2 (NCE2)

<400> SEQUENCE: 6

Met Leu Thr Leu Ala Ser Lys Leu Lys Arg Asp Asp Gly Leu Lys Gly
1               5                   10                  15

Ser Arg Thr Ala Ala Thr Ala Ser Asp Ser Thr Arg Arg Val Ser Val
            20                  25                  30

Arg Asp Lys Leu Leu Val Lys Glu Val Ala Glu Leu Glu Ala Asn Leu
        35                  40                  45

Pro Cys Thr Cys Lys Val His Phe Pro Asp Pro Asn Lys Leu His Cys
    50                  55                  60

Phe Gln Leu Thr Val Thr Pro Asp Glu Gly Tyr Tyr Gln Gly Gly Lys
65                  70                  75                  80

Phe Gln Phe Glu Thr Glu Val Pro Asp Ala Tyr Asn Met Val Pro Pro
                85                  90                  95

Lys Val Lys Cys Leu Thr Lys Ile Trp His Pro Asn Ile Thr Glu Thr
            100                 105                 110

Gly Glu Ile Cys Leu Ser Leu Leu Arg Glu His Ser Ile Asp Gly Thr
        115                 120                 125

Gly Trp Ala Pro Thr Arg Thr Leu Lys Asp Val Val Trp Gly Leu Asn
    130                 135                 140

Ser Leu Phe Thr Asp Leu Leu Asn Phe Asp Asp Pro Leu Asn Ile Glu
145                 150                 155                 160

Ala Ala Glu His His Leu Arg Asp Lys Glu Asp Phe Arg Asn Lys Val
                165                 170                 175

Asp Asp Tyr Ile Lys Arg Tyr Ala Arg
            180                 185
```

<210> SEQ ID NO 7
<211> LENGTH: 552
<212> TYPE: DNA
<213> ORGANISM: Human
<220> FEATURE:
<221> NAME/KEY: misc_feature
<222> LOCATION: (1)..(552)
<223> OTHER INFORMATION: NEDD8-conjugating enzyme 1 (NCE1)

<400> SEQUENCE: 7

```
tactagttcg acaagagcga cttcgtcgtc ttcttcctcc tcctcagccg cccgccgtgg      60
ttcccgtcgt cgttcttccg cagccgccgc gtcgacgcct aggtcttcct gtatttgctc     120
gacttggacg ggtctgcac actatagtcg aagagtctag gtctgctgga ggagttgaag      180
ttcgaccagt agacaggact actcccgaag atgttctcac ccttcaaaca caagtcaaaa     240
ttccacccgg tcccaatggg cgtactaggg gggttccact tcacactctg ttaccagata     300
gtggggttgt aactggagct cccgttgcag acggagttgt aggagtctct cctgaccttc     360
ggtcaggaat gctatttgag gtattaaata ccggacgtca tagagaagaa cctcgggttg     420
gggctcctgg gtgacttgtt cctccggcgt ctccaggacg tcttgttggc cgccgacaaa     480
ctcgtcttgc acgtcgcgag gtacgcccca ccgatgtagc cgaggtggat gaaactcgcg     540
acggacttta tc                                                         552
```

<210> SEQ ID NO 8
<211> LENGTH: 140
<212> TYPE: PRT
<213> ORGANISM: Yeast
<220> FEATURE:
<221> NAME/KEY: MISC_FEATURE
<222> LOCATION: (1)..(188)
<223> OTHER INFORMATION: Yeast Ubc12

<400> SEQUENCE: 8

```
Met Leu Lys Leu Arg Gln Leu Gln Lys Lys Gln Lys Glu Asn Glu
1               5                   10                  15

Asn Ser Ser Ser Ile Gln Pro Asn Leu Ser Ala Ala Arg Ile Arg Leu
                20                  25                  30

Lys Arg Asp Leu Asp Ser Leu Asp Leu Pro Pro Thr Val Thr Leu Asn
            35                  40                  45

Val Ile Thr Ser Pro Asp Ser Ala Asp Arg Ser Gln Ser Pro Lys Leu
        50                  55                  60

Asn Val Cys Leu Asn Ile Leu Arg Glu Asp Trp Ser Pro Ala Leu Asp
65                  70                  75                  80

Leu Gln Ser Ile Ile Thr Gly Leu Leu Phe Leu Phe Leu Glu Pro Asn
                85                  90                  95

Pro Asn Asp Pro Leu Asn Lys Asp Ala Ala Lys Leu Leu Cys Glu Gly
            100                 105                 110

Glu Lys Glu Phe Ala Glu Ala Val Arg Leu Thr Met Ser Gly Gly Ser
        115                 120                 125

Ile Glu His Val Lys Tyr Asp Asn Ile Val Ser Pro
    130                 135                 140
```

<210> SEQ ID NO 9
<211> LENGTH: 558
<212> TYPE: DNA
<213> ORGANISM: Human
<220> FEATURE:
<221> NAME/KEY: misc_feature
<222> LOCATION: (1)..(558)
<223> OTHER INFORMATION: NEDD-conjugating enzyme 2 (NCE2)

<400> SEQUENCE: 9

```
tacgattgcg atcgttcatt tgacttcgca ctgctaccag agtttcccag ggcctgccgt    60
cggtgtcgca ggctgagctg agcctcccaa agacactctc tgtttaacga acaatttctc   120
caacgtcttg aacttcgatt aaatggaaca tgtacatttc acgtaaaagg actaggtttg   180
ttcgaagtaa caaaagtcga ttgtcattgg ggtctactcc caatgatggt cccacctttt   240
aaagtcaaac tttgacttca agggctacgc atgttgtacc acggagggtt tcactttacg   300
gactggttct agaccgtggg gttgtagtgt ctctgtcccc tttatacaga ctcaaataac   360
tctcttgtaa gttaactacc gtgaccgacc cgagggtgtt cttgtaattt cctacagcaa   420 accccctaatt tgagaaacaa atgactagaa aacttaaaac tactaggtga cttataactt   480
cgacgtcttg tagtaaacgc cctgttcctc ctgaaggcct tatttcacct actgatgtag   540
tttgcaatac ggtctact                                                  558
```

<210> SEQ ID NO 10
<211> LENGTH: 180
<212> TYPE: PRT
<213> ORGANISM: Caenorhabditis elegans
<220> FEATURE:
<221> NAME/KEY: MISC_FEATURE
<222> LOCATION: (1)..(180)
<223> OTHER INFORMATION: Ce275850

<400> SEQUENCE: 10

```
Met Phe Asn Leu Gln Lys Arg Ile Asn Gly Asn Asn Glu Asp Gly Arg
1               5                  10                  15

Tyr Leu Glu Thr Arg Ile Ala Val Arg Asp Lys Leu Leu Ala Gln Glu
            20                  25                  30

Leu Gln Gln Leu Glu Thr Ala Leu Arg Asp Gln Lys Gln Lys Leu Trp
        35                  40                  45

His Leu Glu Val Pro Ser Thr Ser Cys Leu His Glu Leu Glu Leu Thr
    50                  55                  60

Val Thr Pro Gln Glu Gly Ile Tyr Arg Gly Gly Lys Phe Arg Phe Lys
65                  70                  75                  80

Ile Thr Val Pro Pro Glu Tyr Asn Asn Val Pro Pro Val Val Lys Cys
                85                  90                  95

Leu Thr Lys Val Trp His Pro Asn Ile Asn Glu Asp Gly Ser Ile Cys
            100                 105                 110

Leu Ser Ile Leu Arg Gln Asn Ser Leu Asp Gln Tyr Gly Trp Arg Pro
        115                 120                 125

Thr Arg Asn Leu Thr Asp Val Val His Gly Leu Val Ser Leu Phe Asn
    130                 135                 140

Asp Leu Met Asp Phe Asn Asp Ala Leu Asn Ile Gln Ala Ala Gln Met
145                 150                 155                 160

Trp Ser Trp Asn Arg Glu Ser Phe Asn His Arg Val Arg Glu Tyr Ile
                165                 170                 175

Ser Arg Tyr Cys
            180
```

<210> SEQ ID NO 11
<211> LENGTH: 200
<212> TYPE: PRT
<213> ORGANISM: Yeast
<220> FEATURE:

```
<221> NAME/KEY: MISC_FEATURE
<222> LOCATION: (1)..(200)
<223> OTHER INFORMATION: UBC1

<400> SEQUENCE: 11
```

| | | | | | | | | | | | | | | | |
|---|---|---|---|---|---|---|---|---|---|---|---|---|---|---|---|
| Met | Ala | Asn | Ile | Ala | Val | Gln | Arg | Ile | Lys | Arg | Glu | Phe | Lys | Glu | Val |
| 1 | | | | 5 | | | | | 10 | | | | | 15 | |
| Leu | Lys | Ser | Glu | Glu | Thr | Ser | Lys | Asn | Gln | Ile | Lys | Val | Asp | Leu | Val |
| | | | | 20 | | | | | 25 | | | | | 30 | |
| Asp | Glu | Asn | Phe | Thr | Glu | Leu | Arg | Gly | Glu | Ile | Ala | Gly | Pro | Pro | Asp |
| | | | 35 | | | | | 40 | | | | | 45 | | |
| Thr | Pro | Tyr | Glu | Gly | Gly | Arg | Tyr | Gln | Leu | Glu | Ile | Lys | Ile | Pro | Glu |
| | | | 50 | | | | | 55 | | | | | 60 | | |
| Thr | Tyr | Pro | Phe | Asn | Pro | Lys | Val | Arg | Phe | Ile | Thr | Lys | Ile | Trp | |
| 65 | | | | | 70 | | | | | 75 | | | | | 80 |
| His | Pro | Asn | Ile | Ser | Ser | Val | Thr | Gly | Ala | Ile | Cys | Leu | Asp | Leu | Leu |
| | | | | 85 | | | | | 90 | | | | | 95 | |
| Lys | Asp | Gln | Trp | Ala | Ala | Ala | Met | Thr | Leu | Arg | Thr | Val | Leu | Leu | Ser |
| | | | | 100 | | | | | 105 | | | | | 110 | |
| Leu | Gln | Ala | Asp | Leu | Ala | Ala | Ala | Glu | Pro | Asp | Asp | Pro | Gln | Asp | Ala |
| | | | 115 | | | | | 120 | | | | | 125 | | |
| Val | Val | Ala | Asn | Gln | Tyr | Lys | Gln | Asn | Pro | Glu | Met | Phe | Lys | Gln | Thr |
| | | | 130 | | | | | 135 | | | | | 140 | | |
| Ala | Arg | Leu | Trp | Ala | His | Val | Tyr | Ala | Gly | Ala | Pro | Val | Ser | Ser | Pro |
| 145 | | | | | 150 | | | | | 155 | | | | | 160 |
| Glu | Tyr | Thr | Lys | Lys | Ile | Glu | Asn | Leu | Cys | Ala | Met | Gly | Phe | Asp | Arg |
| | | | | 165 | | | | | 170 | | | | | 175 | |
| Asn | Ala | Val | Ile | Val | Ala | Leu | Ser | Ser | Lys | Ser | Trp | Asp | Val | Glu | Thr |
| | | | | 180 | | | | | 185 | | | | | 190 | |
| Ala | Thr | Glu | Leu | Leu | Leu | Ser | Asn | | | | | | | | |
| | | | 195 | | | | | 200 | | | | | | | |

```
<210> SEQ ID NO 12
<211> LENGTH: 152
<212> TYPE: PRT
<213> ORGANISM: Human
<220> FEATURE:
<221> NAME/KEY: MISC_FEATURE
<222> LOCATION: (1)..(152)
<223> OTHER INFORMATION: UBC2b

<400> SEQUENCE: 12
```

| | | | | | | | | | | | | | | | |
|---|---|---|---|---|---|---|---|---|---|---|---|---|---|---|---|
| Met | Ser | Thr | Pro | Ala | Arg | Arg | Arg | Leu | Met | Arg | Asp | Phe | Lys | Arg | Leu |
| 1 | | | | 5 | | | | | 10 | | | | | 15 | |
| Gln | Glu | Asp | Pro | Pro | Val | Gly | Val | Ser | Gly | Ala | Pro | Ser | Glu | Asn | Asn |
| | | | | 20 | | | | | 25 | | | | | 30 | |
| Ile | Met | Gln | Trp | Asn | Ala | Val | Ile | Phe | Gly | Pro | Glu | Gly | Thr | Pro | Phe |
| | | | 35 | | | | | 40 | | | | | 45 | | |
| Glu | Asp | Gly | Thr | Phe | Lys | Leu | Val | Ile | Glu | Phe | Ser | Glu | Glu | Tyr | Pro |
| | | | 50 | | | | | 55 | | | | | 60 | | |
| Asn | Lys | Pro | Pro | Thr | Val | Arg | Phe | Val | Ser | Lys | Met | Phe | His | Pro | Asn |
| 65 | | | | | 70 | | | | | 75 | | | | | 80 |
| Val | Tyr | Ala | Asp | Gly | Ser | Ile | Cys | Leu | Asp | Ile | Leu | Gln | Asn | Arg | Trp |
| | | | | 85 | | | | | 90 | | | | | 95 | |
| Ser | Pro | Thr | Tyr | Asp | Val | Ser | Ser | Ile | Leu | Thr | Ser | Ile | Gln | Ser | Asp |
| | | | | 100 | | | | | 105 | | | | | 110 | |
| Leu | Asp | Glu | Pro | Asn | Pro | Asn | Ser | Pro | Ala | Asn | Ser | Gln | Ala | Ala | Gln |

-continued

```
                115                 120                 125
Leu Tyr Gln Glu Asn Lys Arg Glu Tyr Glu Lys Arg Val Ser Ala Ile
        130                 135                 140

Val Ile Gln Ser Trp Asn Asp Ser
145                 150

<210> SEQ ID NO 13
<211> LENGTH: 152
<212> TYPE: PRT
<213> ORGANISM: Human
<220> FEATURE:
<221> NAME/KEY: MISC_FEATURE
<222> LOCATION: (1)..(152)
<223> OTHER INFORMATION: UBC2a

<400> SEQUENCE: 13

Met Ser Thr Pro Ala Arg Arg Arg Leu Met Arg Asp Phe Lys Arg Leu
1               5                   10                  15

Gln Glu Asp Pro Pro Ala Gly Val Ser Gly Ala Pro Ser Glu Asn Asn
                20                  25                  30

Ile Met Val Trp Asn Ala Val Ile Phe Gly Pro Glu Gly Thr Pro Phe
        35                  40                  45

Gly Asp Gly Thr Phe Lys Leu Thr Ile Glu Phe Thr Glu Glu Tyr Pro
    50                  55                  60

Asn Lys Pro Pro Thr Val Arg Phe Val Ser Lys Met Phe His Pro Asn
65                  70                  75                  80

Val Tyr Ala Asp Gly Ser Ile Cys Leu Asp Ile Leu Gln Asn Arg Trp
                85                  90                  95

Ser Pro Thr Tyr Asp Val Ser Ser Ile Leu Thr Ser Ile Gln Ser Asp
            100                 105                 110

Leu Asp Glu Pro Asn Pro Asn Ser Pro Ala Asn Ser Gln Ala Ala Gln
        115                 120                 125

Leu Tyr Gln Glu Asn Lys Arg Glu Tyr Glu Lys Arg Val Ser Ala Ile
    130                 135                 140

Val Ile Gln Ser Trp Arg Asp Cys
145                 150

<210> SEQ ID NO 14
<211> LENGTH: 236
<212> TYPE: PRT
<213> ORGANISM: Human
<220> FEATURE:
<221> NAME/KEY: MISC_FEATURE
<222> LOCATION: (1)..(236)
<223> OTHER INFORMATION: Cdc34a

<400> SEQUENCE: 14

Met Ala Arg Pro Leu Val Pro Ser Ser Gln Lys Ala Leu Leu Leu Glu
1               5                   10                  15

Leu Lys Gly Leu Gln Glu Glu Pro Val Glu Gly Phe Arg Val Thr Leu
                20                  25                  30

Val Asp Glu Gly Asp Leu Tyr Asn Trp Glu Val Ala Ile Phe Gly Pro
        35                  40                  45

Pro Asn Thr Tyr Tyr Glu Gly Gly Tyr Phe Lys Ala Arg Leu Lys Phe
    50                  55                  60

Pro Ile Asp Tyr Pro Tyr Ser Pro Pro Ala Phe Arg Phe Leu Thr Lys
65                  70                  75                  80

Met Trp His Pro Asn Ile Tyr Glu Thr Gly Asp Val Cys Ile Ser Ile
                85                  90                  95
```

```
Leu His Pro Pro Val Asp Asp Pro Gln Ser Gly Glu Leu Pro Ser Glu
            100                 105                 110

Arg Trp Asn Pro Thr Gln Asn Val Arg Thr Ile Leu Leu Ser Val Ile
        115                 120                 125

Ser Asp Leu Asn Glu Pro Asn Thr Phe Ser Pro Ala Asn Val Asp Ala
    130                 135                 140

Ser Val Met Tyr Arg Lys Trp Lys Glu Ser Lys Gly Lys Asp Arg Glu
145                 150                 155                 160

Tyr Thr Asp Ile Ile Arg Lys Gln Val Leu Gly Thr Lys Val Asp Ala
                165                 170                 175

Glu Arg Asp Gly Val Lys Val Pro Thr Thr Leu Ala Glu Tyr Cys Val
            180                 185                 190

Lys Thr Lys Ala Pro Ala Pro Asp Glu Gly Ser Asp Leu Phe Tyr Asp
        195                 200                 205

Asp Tyr Tyr Glu Asp Gly Glu Val Glu Glu Ala Asp Ser Cys Phe
    210                 215                 220

Gly Asp Asp Glu Asp Asp Ser Gly Thr Glu Glu Ser
225                 230                 235

<210> SEQ ID NO 15
<211> LENGTH: 147
<212> TYPE: PRT
<213> ORGANISM: Human
<220> FEATURE:
<221> NAME/KEY: MISC_FEATURE
<222> LOCATION: (1)..(147)
<223> OTHER INFORMATION: UBC5b

<400> SEQUENCE: 15

Met Ala Leu Lys Arg Ile His Lys Glu Leu Asn Asp Leu Ala Arg Asp
1               5                   10                  15

Pro Pro Ala Gln Cys Ser Ala Gly Pro Val Gly Asp Asp Met Phe His
            20                  25                  30

Trp Gln Ala Thr Ile Met Gly Pro Asn Asp Ser Pro Tyr Gln Gly Gly
        35                  40                  45

Val Phe Phe Leu Thr Ile His Phe Pro Thr Asp Tyr Pro Phe Lys Pro
    50                  55                  60

Pro Lys Val Ala Phe Thr Thr Arg Ile Tyr His Pro Asn Ile Asn Ser
65                  70                  75                  80

Asn Gly Ser Ile Cys Leu Asp Ile Leu Arg Ser Gln Trp Ser Pro Ala
                85                  90                  95

Leu Thr Ile Ser Lys Val Leu Leu Ser Ile Cys Ser Leu Leu Cys Asp
            100                 105                 110

Pro Asn Pro Asp Asp Pro Leu Val Pro Glu Ile Ala Arg Ile Tyr Lys
        115                 120                 125

Thr Asp Arg Glu Lys Tyr Asn Arg Ile Ala Arg Glu Trp Thr Gln Lys
    130                 135                 140

Tyr Ala Met
145

<210> SEQ ID NO 16
<211> LENGTH: 147
<212> TYPE: PRT
<213> ORGANISM: Human
<220> FEATURE:
<221> NAME/KEY: MISC_FEATURE
<222> LOCATION: (1)..(147)
<223> OTHER INFORMATION: UBC5c
```

```
<400> SEQUENCE: 16

Met Ala Leu Lys Arg Ile Asn Lys Glu Leu Ser Asp Leu Ala Arg Asp
1               5                   10                  15

Pro Pro Ala Gln Cys Ser Ala Gly Pro Val Gly Asp Asp Met Phe His
            20                  25                  30

Trp Gln Ala Thr Ile Met Gly Pro Asn Asp Ser Pro Tyr Gln Gly Gly
        35                  40                  45

Val Phe Leu Thr Ile His Phe Pro Thr Asp Tyr Pro Phe Lys Pro
    50                  55                  60

Pro Lys Val Ala Phe Thr Thr Arg Ile Tyr His Pro Asn Ile Asn Ser
65                  70                  75                  80

Asn Gly Ser Ile Cys Leu Asp Ile Leu Arg Ser Gln Trp Ser Pro Ala
                85                  90                  95

Leu Thr Ile Ser Lys Val Leu Leu Ser Ile Cys Ser Asp Leu Cys Asp
                100                 105                 110

Pro Asn Pro Asp Asp Pro Leu Val Pro Glu Ile Ala Arg Ile Tyr Lys
            115                 120                 125

Thr Asp Arg Asp Lys Tyr Asn Arg Ile Ser Arg Glu Trp Thr Gln Lys
        130                 135                 140

Tyr Ala Met
145

<210> SEQ ID NO 17
<211> LENGTH: 147
<212> TYPE: PRT
<213> ORGANISM: Human
<220> FEATURE:
<221> NAME/KEY: MISC_FEATURE
<222> LOCATION: (1)..(147)
<223> OTHER INFORMATION: UBC5a

<400> SEQUENCE: 17

Met Ala Leu Lys Arg Ile Gln Lys Glu Leu Ser Asp Leu Gln Arg Asp
1               5                   10                  15

Pro Pro Ala His Cys Ser Ala Gly Pro Val Gly Asp Asp Leu Phe His
            20                  25                  30

Trp Gln Ala Thr Ile Met Gly Pro Pro Asp Ser Ala Tyr Gln Gly Gly
        35                  40                  45

Val Phe Phe Leu Thr Val His Phe Pro Thr Asp Tyr Pro Phe Lys Pro
    50                  55                  60

Pro Lys Ile Ala Phe Thr Thr Lys Ile Tyr His Pro Asn Ile Asn Ser
65                  70                  75                  80

Asn Gly Ser Ile Cys Leu Asp Ile Leu Arg Ser Gln Trp Ser Pro Ala
                85                  90                  95

Leu Thr Val Ser Lys Val Leu Leu Ser Ile Cys Ser Asp Leu Thr Asp
                100                 105                 110

Cys Asn Pro Asp Asp Pro Leu Val Pro Asp Ile Ala Gln Ile Tyr Lys
            115                 120                 125

Ser Asp Lys Glu Lys Tyr Asn Arg His Ala Arg Glu Trp Thr Gln Lys
        130                 135                 140

Tyr Ala Met
145

<210> SEQ ID NO 18
<211> LENGTH: 193
<212> TYPE: PRT
```

```
<213> ORGANISM: Human
<220> FEATURE:
<221> NAME/KEY: MISC_FEATURE
<222> LOCATION: (1)..(193)
<223> OTHER INFORMATION: UbcH6

<400> SEQUENCE: 18
```

Met Ser Asp Asp Ser Arg Ala Ser Thr Ser Ser Ser Ser Ser Ser Ser
1               5                   10                  15

Ser Ser Asn Gln Gln Thr Glu Lys Glu Thr Asn Thr Pro Lys Lys Lys
            20                  25                  30

Glu Ser Lys Val Ser Met Ser Lys Asn Ser Lys Leu Leu Ser Thr Ser
        35                  40                  45

Ala Lys Arg Ile Gln Lys Glu Leu Ala Asp Ile Thr Leu Asp Pro Pro
50                  55                  60

Pro Asn Cys Ser Ala Gly Pro Lys Gly Asp Asn Ile Tyr Glu Trp Arg
65                  70                  75                  80

Ser Thr Ile Leu Gly Pro Pro Gly Ser Val Tyr Glu Gly Gly Val Phe
                85                  90                  95

Phe Leu Asp Ile Thr Phe Thr Pro Glu Tyr Pro Phe Lys Pro Pro Lys
            100                 105                 110

Val Thr Phe Arg Thr Arg Ile Tyr His Cys Asn Ile Asn Ser Gln Gly
        115                 120                 125

Val Ile Cys Leu Asp Ile Leu Lys Asp Asn Trp Ser Pro Ala Leu Thr
130                 135                 140

Ile Ser Lys Val Leu Leu Ser Ile Cys Ser Asp Leu Thr Asp Cys Asn
145                 150                 155                 160

Pro Ala Asp Pro Leu Val Gly Ser Ile Ala Thr Gln Tyr Met Thr Asn
                165                 170                 175

Arg Ala Glu His Asp Arg Met Ala Arg Gln Trp Thr Lys Arg Tyr Ala
            180                 185                 190

Thr

```
<210> SEQ ID NO 19
<211> LENGTH: 154
<212> TYPE: PRT
<213> ORGANISM: Human
<220> FEATURE:
<221> NAME/KEY: MISC_FEATURE
<222> LOCATION: (1)..(154)
<223> OTHER INFORMATION: UbcH7

<400> SEQUENCE: 19
```

Met Ala Ala Ser Arg Arg Leu Met Lys Glu Leu Glu Glu Ile Arg Lys
1               5                   10                  15

Cys Gly Met Lys Asn Phe Arg Asn Ile Gln Val Asp Glu Ala Asn Leu
            20                  25                  30

Leu Thr Trp Gln Gly Leu Ile Val Pro Asp Asn Pro Pro Tyr Asp Lys
        35                  40                  45

Gly Ala Phe Arg Ile Glu Ile Asn Phe Pro Ala Glu Tyr Pro Phe Lys
50                  55                  60

Pro Pro Lys Ile Thr Phe Lys Thr Lys Ile Tyr His Pro Asn Ile Asp
65                  70                  75                  80

Glu Lys Gly Gln Val Cys Leu Pro Val Ile Ser Ala Glu Asn Trp Lys
                85                  90                  95

Pro Ala Thr Lys Thr Asp Gln Val Ile Gln Ser Leu Ile Ala Asp Val
            100                 105                 110

Asn Asp Pro Gln Pro Glu His Pro Leu Arg Ala Asp Leu Ala Glu Glu
            115                 120                 125

Tyr Ser Lys Asp Arg Lys Lys Phe Cys Lys Asn Ala Glu Glu Phe Thr
130                 135                 140

Lys Lys Tyr Gly Glu Lys Arg Pro Val Asp
145                 150

<210> SEQ ID NO 20
<211> LENGTH: 152
<212> TYPE: PRT
<213> ORGANISM: Human
<220> FEATURE:
<221> NAME/KEY: MISC_FEATURE
<222> LOCATION: (1)..(152)
<223> OTHER INFORMATION: UbcH8

<400> SEQUENCE: 20

Met Ala Ser Met Arg Val Val Lys Glu Leu Glu Asp Leu Gln Lys Lys
1               5                   10                  15

Pro Pro Pro Tyr Leu Arg Asn Leu Ser Ser Asp Ala Asn Val Leu
            20                  25                  30

Val Trp His Ala Leu Leu Leu Pro Asp Gln Pro Tyr His Leu Lys
        35                  40                  45

Ala Phe Asn Leu Arg Ile Ser Phe Pro Pro Glu Tyr Pro Phe Lys Pro
    50                  55                  60

Pro Met Ile Lys Phe Thr Thr Lys Ile Tyr His Pro Asn Val Asp Glu
65                  70                  75                  80

Asn Gly Gln Ile Cys Leu Pro Ile Ile Ser Ser Glu Asn Trp Lys Pro
                85                  90                  95

Cys Thr Lys Thr Cys Gln Val Leu Glu Ala Leu Asn Val Asp Val Asn
            100                 105                 110

Arg Pro Asn Ile Arg Glu Pro Leu Arg Met Asp Leu Ala Asp Leu Leu
        115                 120                 125

Thr Gln Asn Pro Glu Leu Phe Arg Lys Asn Ala Glu Glu Phe Thr Leu
    130                 135                 140

Arg Phe Gly Val Asp Arg Pro Ser
145                 150

<210> SEQ ID NO 21
<211> LENGTH: 170
<212> TYPE: PRT
<213> ORGANISM: Human
<220> FEATURE:
<221> NAME/KEY: MISC_FEATURE
<222> LOCATION: (1)..(170)
<223> OTHER INFORMATION: UBE2G

<400> SEQUENCE: 21

Met Thr Glu Leu Gln Ser Ala Leu Leu Leu Arg Arg Gln Leu Ala Glu
1               5                   10                  15

Leu Asn Lys Asn Pro Val Glu Gly Phe Ser Ala Gly Leu Ile Asp Asp
            20                  25                  30

Asn Asp Leu Tyr Arg Trp Glu Val Leu Ile Ile Gly Pro Pro Asp Thr
        35                  40                  45

Leu Tyr Glu Gly Gly Val Phe Lys Ala His Leu Thr Phe Pro Lys Asp
    50                  55                  60

Tyr Pro Leu Arg Pro Pro Lys Met Lys Phe Ile Thr Glu Ile Trp His
65                  70                  75                  80

Pro Asn Val Asp Lys Asn Gly Asp Val Cys Ile Ser Ile Leu His Glu

```
                        85                  90                  95
Pro Gly Glu Asp Lys Tyr Gly Tyr Glu Lys Pro Glu Arg Trp Leu
                100                 105                 110
Pro Ile His Thr Val Glu Thr Ile Met Ile Ser Val Ile Ser Met Leu
            115                 120                 125
Ala Asp Pro Asn Gly Asp Ser Pro Ala Asn Val Asp Ala Ala Lys Glu
    130                 135                 140
Trp Arg Glu Asp Arg Asn Gly Glu Phe Lys Arg Lys Val Ala Arg Cys
145                 150                 155                 160
Val Arg Lys Ser Gln Glu Thr Ala Phe Glu
                165                 170

<210> SEQ ID NO 22
<211> LENGTH: 183
<212> TYPE: PRT
<213> ORGANISM: Human
<220> FEATURE:
<221> NAME/KEY: MISC_FEATURE
<222> LOCATION: (1)..(183)
<223> OTHER INFORMATION: UBCH(8)

<400> SEQUENCE: 22

Met Ser Ser Pro Ser Pro Gly Lys Arg Arg Met Asp Thr Asp Val Val
1               5                   10                  15
Lys Leu Ile Glu Ser Lys His Glu Val Thr Ile Leu Gly Gly Leu Asn
            20                  25                  30
Glu Phe Val Val Lys Phe Tyr Gly Pro Gln Gly Thr Pro Tyr Glu Gly
        35                  40                  45
Gly Val Trp Lys Val Arg Val Asp Leu Pro Asp Lys Tyr Pro Phe Lys
    50                  55                  60
Ser Pro Ser Ile Gly Phe Met Asn Lys Ile Phe His Pro Asn Ile Asp
65                  70                  75                  80
Glu Ala Ser Gly Thr Val Cys Leu Asp Val Ile Asn Gln Thr Trp Thr
                85                  90                  95
Ala Leu Tyr Asp Leu Thr Asn Ile Phe Glu Ser Phe Leu Pro Gln Leu
                100                 105                 110
Leu Ala Tyr Pro Asn Pro Ile Asp Pro Leu Asn Gly Asp Ala Ala Ala
            115                 120                 125
Met Tyr Leu His Arg Pro Glu Glu Tyr Lys Gln Lys Ile Lys Glu Tyr
    130                 135                 140
Ile Gln Lys Tyr Ala Thr Glu Glu Ala Leu Lys Glu Gln Glu Glu Gly
145                 150                 155                 160
Thr Gly Asp Ser Ser Ser Glu Ser Ser Met Ser Asp Phe Ser Glu Asp
                165                 170                 175
Glu Ala Gln Asp Met Glu Leu
            180

<210> SEQ ID NO 23
<211> LENGTH: 158
<212> TYPE: PRT
<213> ORGANISM: Human
<220> FEATURE:
<221> NAME/KEY: MISC_FEATURE
<222> LOCATION: (1)..(158)
<223> OTHER INFORMATION: UBC9

<400> SEQUENCE: 23

Met Ser Gly Ile Ala Leu Ser Arg Leu Ala Gln Glu Arg Lys Ala Trp
1               5                   10                  15
```

```
Arg Lys Asp His Pro Phe Gly Phe Val Ala Val Pro Thr Lys Asn Pro
                 20                  25                  30

Asp Gly Thr Met Asn Leu Met Asn Trp Glu Cys Ala Ile Pro Gly Lys
             35                  40                  45

Lys Gly Thr Pro Trp Glu Gly Leu Phe Lys Leu Arg Met Leu Phe
 50                  55                  60

Lys Asp Asp Tyr Pro Ser Ser Pro Lys Cys Lys Phe Glu Pro Pro
 65                  70                  75                  80

Leu Phe His Pro Asn Val Tyr Pro Ser Gly Thr Val Cys Leu Ser Ile
                 85                  90                  95

Leu Glu Glu Asp Lys Asp Trp Arg Pro Ala Ile Thr Ile Lys Gln Ile
                100                 105                 110

Leu Leu Gly Ile Gln Glu Asp Leu Asn Glu Pro Asn Ile Gln Asp Pro
            115                 120                 125

Ala Gln Ala Glu Ala Tyr Thr Ile Tyr Cys Gln Asn Arg Val Glu Tyr
            130                 135                 140

Glu Lys Arg Val Arg Ala Gln Ala Lys Lys Phe Ala Pro Ser
145                 150                 155

<210> SEQ ID NO 24
<211> LENGTH: 180
<212> TYPE: PRT
<213> ORGANISM: Human
<220> FEATURE:
<221> NAME/KEY: MISC_FEATURE
<222> LOCATION: (1)..(180)
<223> OTHER INFORMATION: UBCH10

<400> SEQUENCE: 24

Met Ala Ser Gln Asn Arg Asp Pro Ala Ala Thr Ser Val Ala Ala Ala
 1               5                  10                  15

Ala Arg Lys Gly Ala Glu Pro Ser Gly Gly Ala Ala Arg Gly Pro Val
             20                  25                  30

Gly Lys Arg Leu Gln Gln Glu Leu Met Thr Leu Met Met Ser Gly Asp
             35                  40                  45

Lys Gly Ile Ser Ala Phe Pro Glu Ser Asp Asn Leu Phe Lys Trp Val
 50                  55                  60

Gly Thr Ile His Gly Ala Ala Gly Thr Val Tyr Glu Asp Leu Arg Tyr
 65                  70                  75                  80

Lys Leu Ser Leu Glu Phe Pro Ser Gly Tyr Pro Tyr Asn Ala Pro Thr
                 85                  90                  95

Val Lys Phe Leu Thr Pro Cys Tyr His Pro Asn Val Asp Thr Gln Gly
                100                 105                 110

Asn Ile Cys Leu Asp Ile Leu Lys Glu Lys Trp Ser Ala Leu Tyr Asp
            115                 120                 125

Val Arg Thr Ile Leu Leu Ser Ile Gln Ser Asp Leu Gly Glu Pro Asn
130                 135                 140

Ile Asp Ser Pro Leu Asn Thr His Ala Ala Glu Leu Trp Lys Asn Pro
145                 150                 155                 160

Thr Ala Phe Lys Lys Tyr Leu Gln Glu Thr Tyr Ser Lys Gln Val Thr
                165                 170                 175

Ser Gln Glu Pro
            180

<210> SEQ ID NO 25
<211> LENGTH: 152
```

```
<212> TYPE: PRT
<213> ORGANISM: Human
<220> FEATURE:
<221> NAME/KEY: MISC_FEATURE
<222> LOCATION: (1)..(152)
<223> OTHER INFORMATION: UBC 13

<400> SEQUENCE: 25

Met Ala Gly Leu Pro Arg Arg Ile Ile Lys Glu Thr Gln Arg Leu Leu
1               5                   10                  15

Ala Glu Pro Val Pro Gly Ile Lys Ala Glu Pro Asp Glu Ser Asn Ala
            20                  25                  30

Arg Tyr Phe His Val Val Ile Ala Gly Pro Gln Asp Ser Pro Phe Glu
        35                  40                  45

Gly Gly Thr Phe Lys Leu Glu Leu Phe Leu Pro Glu Glu Tyr Pro Met
50                  55                  60

Ala Ala Pro Lys Val Arg Phe Met Thr Lys Ile Tyr His Pro Asn Val
65                  70                  75                  80

Asp Lys Leu Gly Arg Ile Cys Leu Asp Ile Leu Lys Asp Glu Trp Ser
                85                  90                  95

Pro Ala Leu Gln Ile Arg Thr Val Leu Leu Ser Ile Gln Ala Asp Leu
            100                 105                 110

Ser Ala Pro Asn Pro Asp Asp Pro Leu Ala Asn Asp Val Ala Glu Gln
        115                 120                 125

Trp Lys Thr Asn Glu Ala Gln Ala Ile Glu Thr Ala Arg Ala Trp Thr
130                 135                 140

Arg Leu Tyr Ala Met Asn Asn Ile
145                 150

<210> SEQ ID NO 26
<211> LENGTH: 14
<212> TYPE: PRT
<213> ORGANISM: Artificial Sequence
<220> FEATURE:
<223> OTHER INFORMATION: Tryptic peptide sequence for p60
<221> NAME/KEY: MISC_FEATURE
<222> LOCATION: (11)..(13)
<223> OTHER INFORMATION: Amino acids 11 and 13 are Xaa wherein Xaa = any
      amino acid.

<400> SEQUENCE: 26

Phe Thr Val Val Ala Thr Gln Leu Pro Glu Xaa Thr Xaa Leu
1               5                   10

<210> SEQ ID NO 27
<211> LENGTH: 12
<212> TYPE: PRT
<213> ORGANISM: Artificial Sequence
<220> FEATURE:
<223> OTHER INFORMATION: Tryptic peptide sequence for p60

<400> SEQUENCE: 27

Glu His Phe Gln Ser Tyr Asp Leu Asp His Met Glu
1               5                   10

<210> SEQ ID NO 28
<211> LENGTH: 9
<212> TYPE: PRT
<213> ORGANISM: Artificial Sequence
<220> FEATURE:
<223> OTHER INFORMATION: Tryptic peptide sequence for p60

<400> SEQUENCE: 28
```

Gln Thr Pro Ser Phe Trp Ile Leu Ala
1               5

<210> SEQ ID NO 29
<211> LENGTH: 24
<212> TYPE: DNA
<213> ORGANISM: Human

<400> SEQUENCE: 29
gcaggatgat caagctgttc tcgc                                              24

<210> SEQ ID NO 30
<211> LENGTH: 24
<212> TYPE: DNA
<213> ORGANISM: Human

<400> SEQUENCE: 30
cgtggcgggg gtgggtatgc gcca                                              24

<210> SEQ ID NO 31
<211> LENGTH: 33
<212> TYPE: DNA
<213> ORGANISM: Human

<400> SEQUENCE: 31
cgggaattcc atatgatcaa gctgttctcg ctg                                    33

<210> SEQ ID NO 32
<211> LENGTH: 33
<212> TYPE: DNA
<213> ORGANISM: Human

<400> SEQUENCE: 32
cgcccaagct tctatttcag gcagcgctca aag                                    33

<210> SEQ ID NO 33
<211> LENGTH: 7
<212> TYPE: PRT
<213> ORGANISM: Artificial Sequence
<220> FEATURE:
<223> OTHER INFORMATION: N-terminus of NCE1

<400> SEQUENCE: 33

Met His His His His His His
1               5

<210> SEQ ID NO 34
<211> LENGTH: 24
<212> TYPE: PRT
<213> ORGANISM: Human

<400> SEQUENCE: 34

His Pro Asn Ile Thr Glu Thr Ile Cys Leu Ser Leu Leu Arg Glu His
1               5                   10                  15

Ser Ile Asp Gly Thr Gly Trp Ala
                20

<210> SEQ ID NO 35
<211> LENGTH: 20
<212> TYPE: DNA
<213> ORGANISM: Human

<400> SEQUENCE: 35
agcccagggt aaaggcagca                                                   20

```
<210> SEQ ID NO 36
<211> LENGTH: 20
<212> TYPE: DNA
<213> ORGANISM: Human

<400> SEQUENCE: 36
catgttagag acaaactgta                                              20

<210> SEQ ID NO 37
<211> LENGTH: 31
<212> TYPE: DNA
<213> ORGANISM: Human

<400> SEQUENCE: 37
gggaattcca tatgctaacg ctagcaagta a                                 31

<210> SEQ ID NO 38
<211> LENGTH: 28
<212> TYPE: DNA
<213> ORGANISM: Human

<400> SEQUENCE: 38
ccatcgattc atctggcata acgtttga                                     28
```

1

HUMAN PROTEINS RESPONSIBLE FOR NEDD8 ACTIVATION AND CONJUGATION

This application is a continuation-in-part of provisional application Ser. No. 60/068,029, filed Dec. 19, 1997, and a continuation-in-part of provisional application Ser. No. 60/096,525, filed Aug. 12, 1998.

This invention was supported in part by grant number GM53136 from National Institute of Health. The government has certain rights in this invention.

BACKGROUND OF THE INVENTION

1. Field of the Invention

The invention relates to covalent modification of proteins through their conjugation with other proteins. More particularly, the invention relates to the modulation of such conjugation involving the protein NEDD8.

2. Summary of the Related Art

Covalent modification of proteins through their conjugation with other proteins is an important biological mechanism for regulating protein metabolism and biological activity. Hershko and Ciechanover, Annu. Rev. Biochem. 61: 761–807 (1992) discloses conjugation of ubiquitin, one of the most conserved eukaryotic proteins, to other proteins through an enzymatic mechanism, as well as its role in protein degradation. Rock et al., Cell 78: 761–771 (1994) discloses that ubiquitination of protein antigens is required for processing of such antigens. Murray, Cell 81: 149–152 (1995), teaches that ubiquitination of cyclin is involved in cell cycle regulation. Scheffner et al., Cell 75: 495–505 (1993) discloses that ubiquitination of p53 is involved in degradation of this tumor suppressor.

The enzymatic pathway for ubiquitination has been reasonably well defined jentsch, Annu. Rev. Genet. 26: 179–207 (1992) discloses that ubiquitination requires initial activation of a conserved C-terminal glycine residue by the ubiquitin activating enzyme, E1, through formation of ubiquitin adenylate in an ATP-dependent process which liberates PPi, followed by thiol ester formation at a thiol site in E1 with release of AMP. Ubiquitin is then transferred to a thiol site in ubiquitin conjugating enzyme, E2, through formation of a thiol ester bond. Ubiquitin is then transferred to an epsilon amino group of a lysine residue in the target protein through an amide linkage, usually with the involvement ofubiquitin-protein isopeptide ligase, E3. Hopkin J. Natl. Inst. Health Res. 9: 36–42 (1997), teaches that target specificity is regulated by the particular combination of E2 and E3 protein with more than 30 E2 proteins and 10 E3 proteins being known at present.

Ubiquitin is not the only protein which is used to modify other proteins through covalent linkage, however. Kamitani et al., J. Biol. Chem. 272: 14001–14004 (1997), discloses the sentrin, a ubiquitin-like protein, appears to be processed similarly to ubiquitin, but has a smaller target protein repertoire than ubiquitin. Okura et al., J. Immunol. 272: 4277–4281 (1986) teaches that sentrin protects cells against anti-FAS and tumor necrosis factor-mediated cell death. Loeb and Haas, J. Biol. Chem. 267: 7806–7813 (1982), discloses that ubiquitin cross-reactive protein (UCRP), which contains two ubiquitin domains, is conjugated to a large number of intracellular proteins. Kumar et al., Biochem. Biophys. Res. Commun. 185: 1155–1161 (1992), discloses another ubiquitin-like protein, called NEDD8, for Neural precursor cell-Expressed Developmentally Down regulated. Kamitani et al., J. Biol. Chem. 272: 28557–28562 (1997), teaches that NEDD8 is predominantly expressed in the nucleus and is conjugated to target proteins through a mechanism analogous to ubiquitination.

These proteins, which covalently modify other cellular proteins, are important components of biological regulatory processes. The nuclear expression pattern and developmental regulation of NEDD8 make it a particularly compelling candidate as an important regulatory molecule. There is a need, therefore to understand the role of NEDD8 in biological regulation. Unfortunately, the lack of understanding about the specific proteins involved in NEDD8 conjugation has resulted in a lack of effective tools to probe the role of NEDD8. There is, therefore, a need for better tools to utilize in elucidating the role of NEDD8 in biological regulation. Ideally, such tools would allow modulation of the activation and/or conjugation of NEDD8.

BRIEF SUMMARY OF THE INVENTION

The invention provides compositions and methods for detecting and/or modulating the conjugation of NEDD8 and/or its transfer to a target protein, as well as compositions and methods for discovering molecules which are useful in detecting and/or modulating the conjugation of NEDD8 and/or its transfer to a target protein. The present invention arises from the purification and characterization of novel NEDD8 activating and conjugating enzymes.

In a first aspect, the invention provides purified NEDD8-activating protein beta subunit (NAE1-beta). The primary amino acid sequence of a preferred embodiment of such NAE1-beta protein is shown in FIG. 1.

A second aspect, the invention provides NAE1-beta expression elements Such elements include, without limitation, isolated of recombinant nucleic acid sequences encoding NAE1-beta or nucleic acid sequences specifically homologous or specifically complementary thereto, vectors comprising any such nucleic acid sequences and recombinant expression units which express NAE1-beta, or, antisense transcripts or dominant negative mutants thereof.

The purified protein and its structural information provided herein enables the preparation of NAE1-beta-binding molecules (NAE1BBMs). Thus, in a third aspect, the invention provides methods for identifying NAE1BBMs. One preferred method according to this aspect of the invention comprises screening for NAE1BBMs by contacting purified NAE1-beta according to the invention and populations of molecules or mixed populations of molecules and determining the presence of molecules which bind specifically to NAE1-beta. Another preferred method according to this aspect of the invention comprises rationally designing molecules to bind NAE1-beta based upon structural information from the purified NAE1-beta protein provided by the invention and determining whether such rationally designed molecules bind specifically to NAE1-beta. This aspect of the invention includes NAE1BBMs identified by the methods according to the invention.

NAE1BBMs can be used in conventional assays to detect the presence or absence, and/or quantity of NAE1-beta, NAE1 heterodimer, or NAE1 heterodimer/NEDD8 complex in a biological sample. Thus, in a fourth aspect, the invention provides methods for determining the presence or absence and/or quantity of NAE1-beta, NAE1 heterodimer, or NAE1 heterodimer/NEDD8 complex in a biological sample. Such methods comprise providing a detectable NAE1BBM to a biological sample, allowing the detectable NAE1BBM to bind to NAE1-beta, NAE1 heterodimer, or NAE1 heterodimer/NEDD8 complex, if any is present in the biological sample, and detecting the presence or absence and/or quantity of a complex of the detectable NAE1BBM and NAE1-beta, NAE1-heterodimer, or NAE1 heterodimer/NEDD8 complex.

Nucleic acid sequences specifically complementary to and/or specifically homologous to nucleic acid sequences encoding NAE1-beta can also be used in conventional assays to detect the presence or absence of NAE1-beta nucleic acid in a biological sample. Thus, in a fifth aspect, the invention provides methods for determining the presence or absence and/or quantity of NAE1-beta nucleic acid in a biological sample. In preferred embodiments, such assays are nucleic acid hybridization and/or amplification assay, such assays comprising providing to the biological sample a nucleic acid sequence which is specifically complementary to NAE1-beta nucleic acid.

In a sixth aspect, the invention provides methods for identifying modulating ligands of NAE1-beta. Some NAE1BBMs are capable of acting as antagonists or agonists of NAE1-beta. Thus, the method according to this aspect of the invention comprises providing NAE1BBMs to an assay system for NAE1-beta participation in the NEDD8-activation/conjugation pathway, and determining whether such NAE1BBMs interfere with or enhance the ability of NAE1-beta to participate in the NEDD8-activation/conjugation pathway. The NAE1BBMs are preferably provided as a population of molecules (most preferably rationally designed molecules), or as a mixed population of molecules, as for example in a screening procedure. This aspect of the invention includes modulating ligands of NAE1-beta identified by this method according to the invention.

In a seventh aspect, the invention provides modulating ligands of NAE1-beta. Preferred modulating ligands are NAE1BBMs which act as antagonists, interfering with the ability of NAE1-beta to participate in the NEDD8-activation/conjugation pathway. Other preferred modulating ligands are NAE1BBMs which act as agonists, enhancing the ability of NAE1-beta to participate in the NEDD8-activation/conjugation pathway. In certain embodiments, such NAE1BBMs preferably interact with NAE1-beta to inhibit or enhance the formation of NAE1 heterodimer, the formation of NEDD8 adenylate, the formation of a thiol ester bond between NEDD8 and NAE1, and/or transfer of NEDD8 to NEDD8-conjugating enzyme.

In an eighth aspect, the invention provides methods for modulating the activation and/or conjugation of NEDD8. One preferred embodiment of the method according to this aspect of the invention comprises providing a modulating ligand of NAE1-beta or a recombinant expression unit which expresses NAE1-beta or an antagonist thereof to a biological system in which NEDD8 is conjugated to another protein.

In a ninth aspect, the invention provides oligonucleotides that are specifically complementary to a portion of a nucleotide sequence shown in FIG. 1. Preferred embodiments include hybridization probes and antisense oligonucleotides.

In a tenth aspect, the invention provides methods for identifying NAE1-alpha binding molecules (NAE1ABMs). The present inventors have identified the alpha subunit of the NAE1 heterodimer (NAE1-alpha). Surprisingly, it has an amino acid sequence which is substantially identical to a protein previously identified as amyloid precursor protein binding protein 1 (APP-BP1; see Chow et al., J. Biol. Chem. 271: 11339–11346 (1996)). One preferred method according to this aspect of the invention comprises screening for NAE1ABMs by contacting purified NAE1-alpha and populations of molecules or mixed populations of molecules and determining the presence of molecules which bind specifically to NAE1-alpha. Another preferred method according to this aspect of the invention comprises rationally designing molecules to bind NAE1-alpha based upon structural information from the NAE1-alpha protein identified by the present inventors and determining whether such rationally designed molecules bind specifically to NAE1-alpha. This aspect of the invention includes NAE1ABMs identified by the methods according to the invention.

NAE1ABMs cn be used in conventional assays to detect the presence or absence, and/or quantity of NAE1-alpha, NAE1 heterodimer, or NAE1 heterodimer/NEDD8 complex in a biological sample. Thus, in an eleventh aspect, the invention provides methods for determining the presence of absence and/or quantity of NAE1-alpha, NAE1 heterodimer, or NAE1 heterodimer/NEDD8 complex in a biological sample. Such methods comprise providing a detectable NAE1ABM to a biological sample, allowing the detectable NAE1ABM to bind to NAE1-alpha, NAE1 heterodimer, or NAE1 heterodimer/NEDD8 complex, if any is present in the biological sample, and detecting the presence or absence and/or quantity of a complex of the detectable NAE1ABM and NAE1-alpha, NAE1-heterodimer, or NAE1 heterodimer/NEDD8 complex. In preferred embodiments, the method according to this aspect of the invention is used to detect the presence or absence, and/or quantity of NAE1 heterodimer or NAE1 heterodimer/NEDD8 complex in a biological sample.

Nucleic acid sequences specifically complementary to and/or specifically homologous to nucleic acid sequences encoding NAE1-alpha can also be used in conventional assays to detect the presence or absence of NAE1-alpha nucleic acid in a biological sample in which NEDD8 conjugation is suspected. Thus, in a twelfth aspect, the invention provides methods for determining the presence or absence and/or quantity of NAE1-alpha nucleic acid in such a biological sample. In preferred embodiments, such assays are nucleic acid hybridization and/or amplification assays, such assays comprising providing to the biological sample a nucleic acid sequence which is specifically complementary to NAE1-alpha nucleic acid.

In an thirteenth aspect, the invention provides methods for identifying modulating ligands of NAE1-alpha. Some NAE1ABMs are capable of acting as antagonists or agonists of NAE1-alpha. Thus, the method according to this aspect of the invention comprises providing NAE1ABMs to an assay system for NAE1-alpha participation in the NEDD8-activation/conjugation pathway, and determining whether such NAE1ABMs interfere with or enhance the ability of NAE1-alpha to participate in the NEDD8-activation/conjugation pathway. The NAE1ABMs are preferably provided as a population of molecules (most preferably rationally designed molecules), or as a mixed population of molecules, as for example in a screening procedure. This aspect of the invention includes antagonists or agonists of NAE1-alpha identified by this method according to the invention.

In a fourteenth aspect the invention provides a purified complex of NAE1-beta and NAE1-alpha, or of NAE1-beta, NAE1-alpha and NEDD8, or a purified complex of portions thereof.

In a fifteenth aspect, the invention provides modulating ligands of NAE1-alpha. Certain preferred modulating ligands are NAE1ABMs which act as antagonists which interfere with the ability of NAE1-alpha to participate in the NEDD8-activation/conjugation pathway. Other preferred modulating ligands are NAE1ABMs which act as agonists which enhance the ability of NAE1-alpha to participate in the NEDD8-activation/conjugation pathway. Preferably, such inhibition or enhancement is specific, as described above. In certain embodiments, such modulating ligands preferably interact with NAE1-alpha to inhibit or enhance the formation of NAE1 heterodimer, the formation of NEDD8 adenylate, the formation of a thiol ester bond between NEDD8 and NAE1, and/or transfer of NEDD8 to NEDD8-conjugating enzyme.

In a sixteenth aspect, the invention provides methods for modulating the activation and/or conjugation of NEDD8. One preferred embodiment of the method according to this aspect of the invention comprises providing a modulating ligand NAE1-alpha or a recombinant expression unit which expresses NAE1-alpha or an antagonist thereof to a biological system in which NEDD8 is conjugated to another protein.

In a seventeenth aspect, the invention provides alleic varients of NAE-1 alpha. This aspect of the invention further includes NAE1-alpha allelic variant expression elements. Such elements include, without limitation, isolated or recombinant nucleic acid sequences encoding NAE1-alpha, or nucleic acid sequences specifically homologous or specifically complementary thereto, vectors comprising any such nucleic acid sequences, and recombinant expression units which express NAE1-beta or antisense transcripts or dominant negative mutants thereof.

In a eighteenth aspect, the invention provides methods for modulating auxin response in plants. The present inventors have discovered that NAE1-alpha shares 39% identity and 61% conserved residues with Aux1 in *A. Thaliana,* which is involved in signal transduction in the auxin response in plants. This suggests that antagonists of NAE1-beta and/or NAE1-alpha should down-regulate the auxin response, and that expression of NAE1-beta and/or NAE1-alpha should up-regulate the auxin response. One preferred embodiment of the method according to this aspect of the invention comprises providing a modulating ligand of NAE1-beta or NAE1-alpha or a recombinant expression unit which expresses NAE1-beta or NAE1 or an antagonist thereof to a plant that is under auxin treatment.

In a nineteenth aspect, the invention provides methods for modulating the biological role of APP and/or beta peptide accumulation in a biological system. The present inventors have discovered that NAE1-alpha is substantially the same protein is amyloid precursor protein binding protein-1 (APP-BP1). This suggests that antagonists or agonists of NAE1-beta and/or NAE1-alpha should modulate APP function, including its role in beta peptide accumulation. One preferred embodiment of the method according to this aspect of the invention comprises providing a modulating ligand of NAE1-beta or NAE1-alpha or a recombinant expression unit which expresses NAE1-beta or NAE1 or an antagonist thereof to a biological system.

In an twentieth aspect, the invention provides two new purified NEDD8-conjugating enzymes and allelic variants thereof. The primary amino acid sequence of a preferred embodiment of a first such NEDD8-conjugating enzyme (NCE1) is shown in FIG. 2. The primary amino acid sequence of a preferred embodiment of a second such NEDD8-conjugating enzyme (NCE2) is shown in FIG. 5.

In a twenty-first aspect, the invention provides NEDD8-conjugation enzyme expression elements. Such elements include, without limitation, isolated or recombinant nucleic acid sequences encoding NCE1 or NCE2 or dominant negative mutants thereof, or capable of expressing antisense transcripts thereof or nucleic acid sequences specifically homologous or specifically complementary thereto, and vectors comprising any such recombinant expression elements, preferably expression vectors.

The purified protein and is structural information provided herein enables the preparation of NCE1 and NCE2 binding molecules, respectively NCE1BMs and NCE2BMs. Thus, in a twenty-second aspect, the invention provides methods for identifying NCE1BMs and NCE2BMs. One preferred method according to this aspect of the invention comprises screening for NCE1BMs or NCE2BMs by contacting purified NCE1 or NCE2 according to the invention and populations of molecules or mixed populations of molecules and determining the presence of molecules which bind specifically to NCE1 or NCE2. Another preferred method according to this aspect of the invention comprises rationally designing molecules to bind NCE1 or NCE2 based upon structural information from the purified NCE1 and NCE2 provided by the invention and determining whether such rationally designed molecules bind specifically to NCE1 to NCE2. This aspect of the invention includes NCE1BMs and NCE2BMs identified by the method according to the invention.

NCE1BMs and NCE2BMs can be used in conventional assays to detect the presence or absence, and/or quantity of NCE1 or NCE2, or NCE1 or NCE2/NEDD8 complex in a biological sample. Thus, in a twenty-third aspect, the invention provides methods for determining the presence or absence and/or quantity of NCE1 or NCE2, or NCE1 or NCE2/NEDD8 complex in a biological sample. Such methods comprise providing a detectable NCE1BM or NCE2BM to a biological sample, allowing the detectable NCE1BM or NCE2BM to bind to, respectively NCE1 or NCE2, or respectively NCE1 or NCE2/NEDD8 complex, if any is present in biological sample, and detecting the presence or absence and/or quantity of a complex of the detectable NCE1BM or NCE2BM and NCE1 or NCE2, or NCE1 or NCE2/NEDD8 complex.

Nucleic acid sequences specifically complementary to and/or specifically homologous to nucleic acid sequences encoding NCE1to NCE2 can also be used in conventional assays to detect the presence or absence of NCE1 or NCE2 nucleic acid in a biological sample. Thus, in a twenty-fourth aspect, the invention provides methods for determining the presence or absence and/or quantity of NCE1 or NCE2 nucleic acid in a biological sample. In preferred embodiments, such assays are nucleic acid hybridization and/or amplification assays, such assays comprising providing to the biological sample a nucleic acid sequence which is specifically complementary to NCE1 or NCE2 nucleic acid.

In a twenty-fifth aspect, the invention provides methods for identifying modulating ligands of NCE1 or NCE2. Some NCE1BMs or NCE2BMs are capable of acting as antagonists or agonists of, respectively NCE1 or NCE2. Thus, the method according to this aspect of the invention comprises providing NCE1BMs or NCE2BMs to an assay system for NCE1 or NCE2 participation in the NEDD8-activation/conjugation pathway, and determining whether such NCE1BMs or NCE2BMs interfere with or enhance the ability of NCE1 or NCE2 to participate in the NEDD8-activation/conjugation pathway. The NCE1BMs or NCE2BMs are preferably provided as a population of molecules (most preferably rationally designed molecules), or as a mixed population of molecules, as for example in a screening procedure. This aspect of the invention includes modulating ligands of NCE1 or NCE2 identified by this invention according to the invention.

In a twenty-sixth aspect, the invention provides modulating ligands of NCE1or NCE2. Preferred modulating ligands are NCE1BMs or NCE2BMs which act as antagonists, interfering with the ability of NCE1 or NCE2 to participate in the NEDD8-activation/conjugation pathway. Other preferred modulating ligands are NCE1BMs or NCE2BMs which act as agonists, enhancing the ability of, respectively NCE1 or NCE2 to participate in the NEDD8-activation/conjugation pathway. In certain embodiments, such NCE1BMs or NCE2BMs preferably interact with NCE1 or NCE2 to inhibit or enhance the formation of a thiol ester bond between NEDD8 and NCE1 to NCE2 and/or transfer of NEDD8 to its target protein.

In a twenty-seventh aspect, the invention provides methods for modulating the conjugation of NEDD8 or its transfer to a target protein. One preferred embodiment of the method according to this aspect of the invention comprises providing a modulating ligand of NCE1 or NCE2 or a recombinant expression unit which expresses NCE1 or NCE2 or an antagonist thereof to a biological system in which NEDD8 is conjugated to another protein.

In a twenty-eighth aspect, the invention provides oligonucleotides that are specifically complementary to a portion of a nucleotide sequence shown in FIG. 2 or FIG. 5. Preferred embodiments include hybridization probes and antisense oligonucleotides.

BRIEF DESCRIPTION OF THE DRAWINGS

FIG. 1 shows the nucleotide [SEQ. ID. NO. 1] and predicted amino acid sequence [SEQ. ID. NO. 2] for NAE1-beta, with the two tryptic peptide sequences highlighted by underline.

FIG. 2 shows the nucleotide [SEQ. ID. NO. 3] and predicted amino acid sequence [SEQ. ID. NO. 4] for NEDD8 -conjugating enzyme 1 (NCE1), with the active Cys residue indicated.

FIG. 3 shows the alignment of NCE1 with yeast Ubc12.

FIG. 5 shows the nucleotide [SEQ. ID. NO.5] and predicted amino acid sequence [SEQ. ID. NO. 6] for NEDD-8-conjugating enzyme 2 (NCE2) with the active Cys residue indicated.

FIG. 6 shows homology between NCE2 and a *C. elegans* gene of unknown function.

Figure 7A:
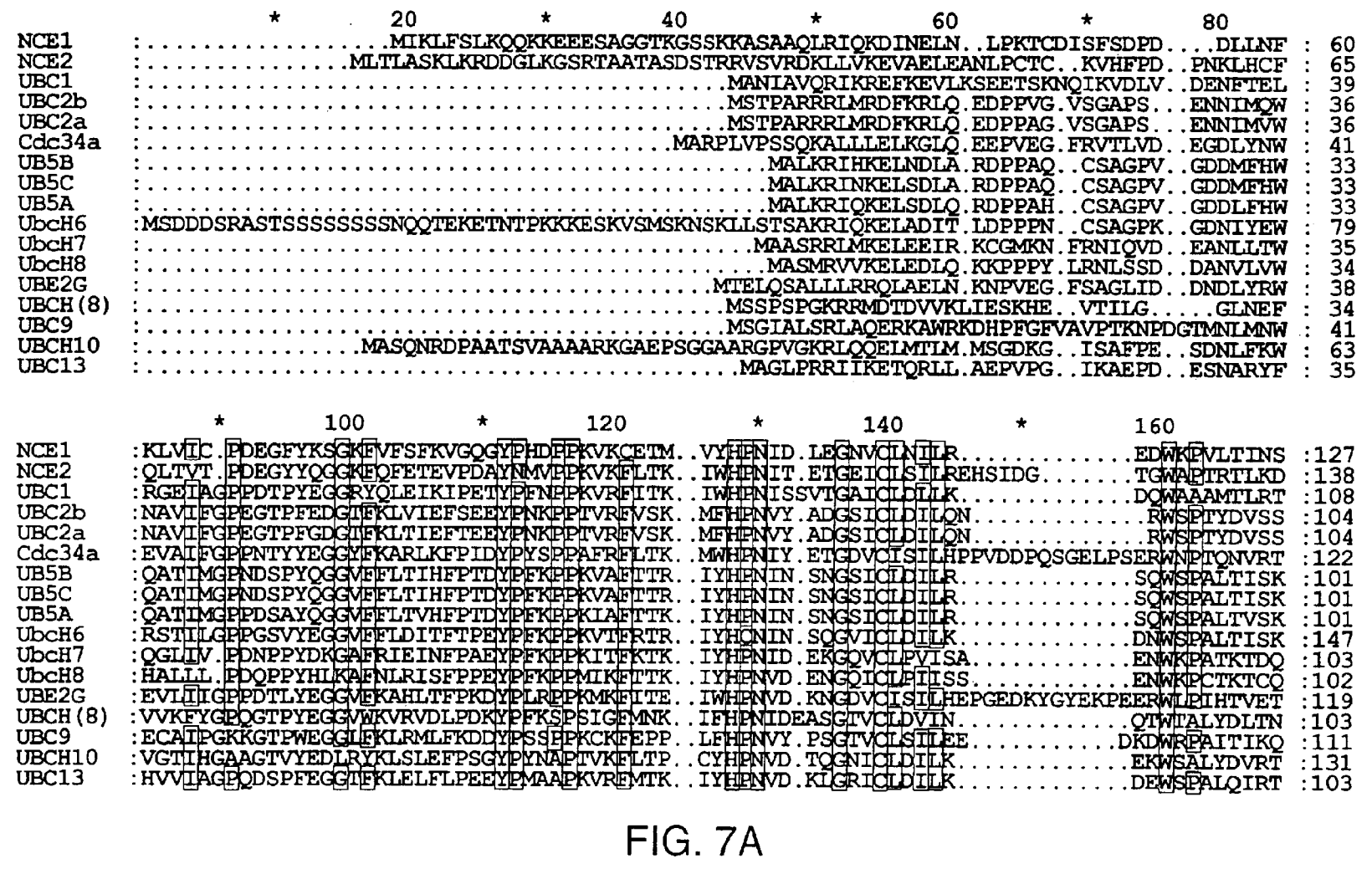
Figure 7B:
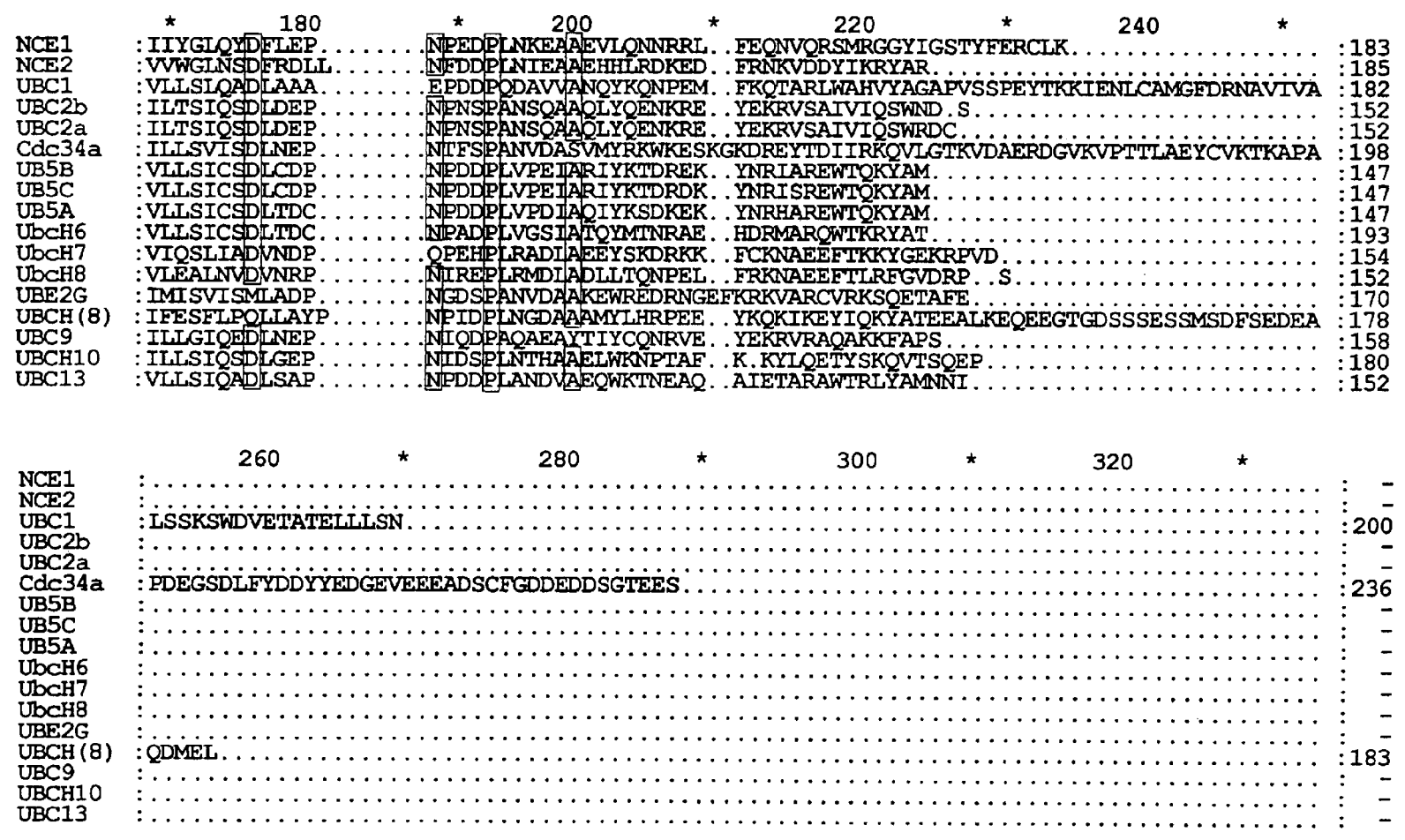

FIG. 7 shows the sequence alignment of NCE1 and NCE2 with known Ubc proteins.

DETAILED DESCRIPTION OF THE PREFERRED EMBODIMENTS

Figure 4:
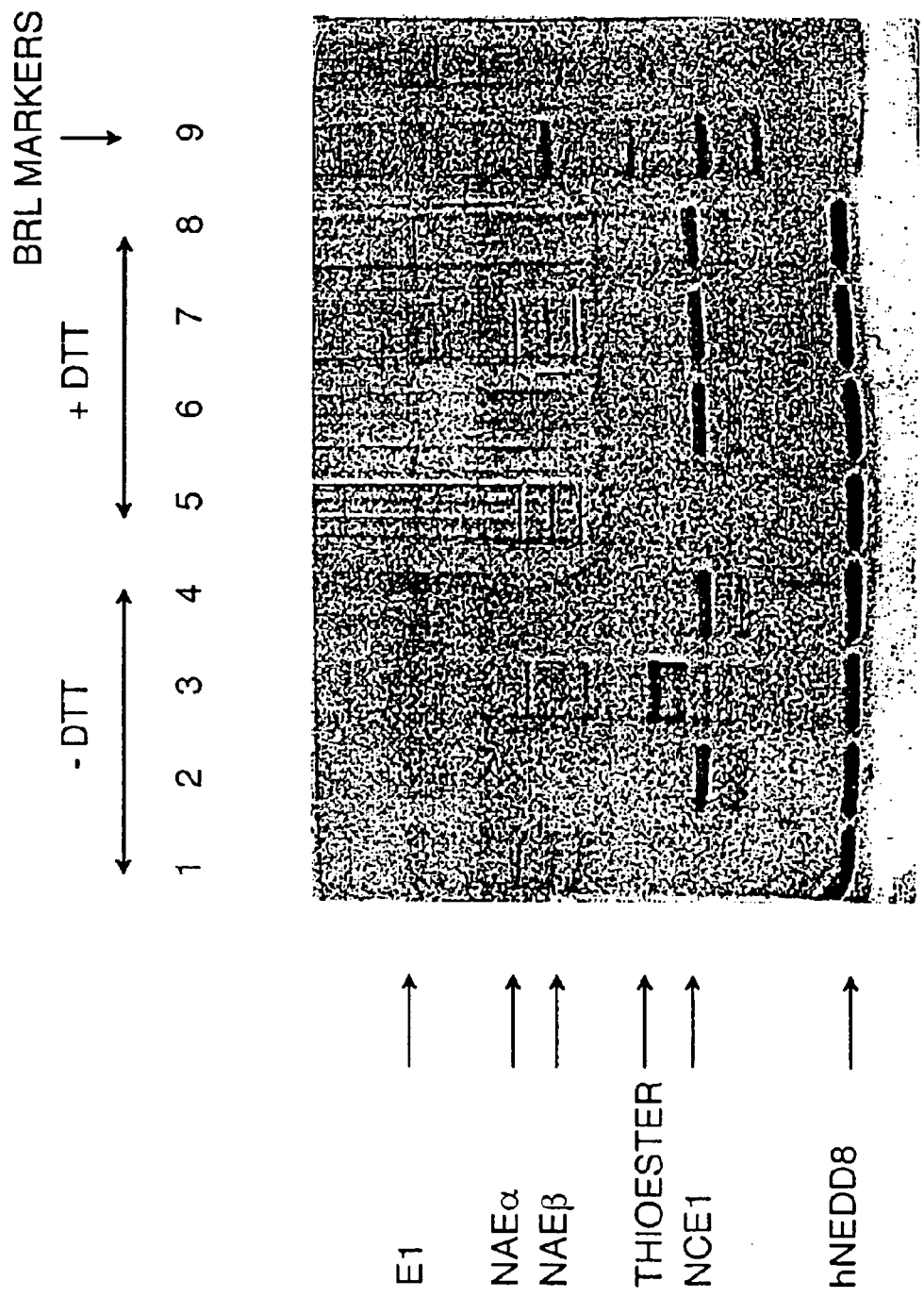
FIG. 4 shows results of an assay for thioester bond formation between NEDD-8 and NCE1.
Figures 7C, 8:
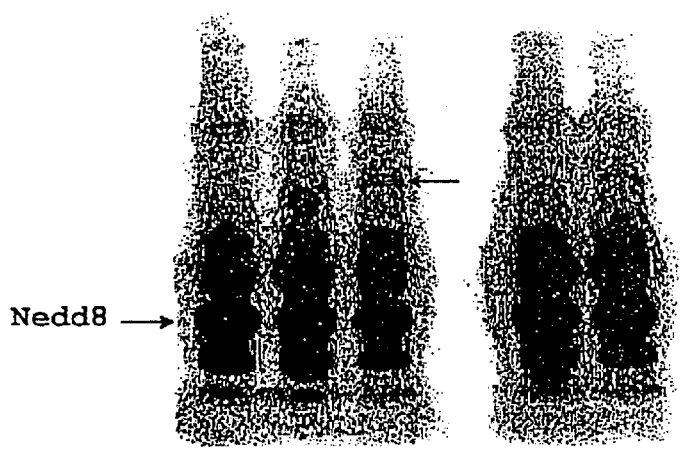
FIG. 8 shows results of an assay for thioester bond formation between NEDD8 and NCE2.

The invention relates to covalent modification of proteins through their conjugation with other proteins. More particularly, the invention relates to the modulation of such conjugation involving the protein NEDD8. The invention provides compositions and methods for detecting and/or modulating the conjugation of NEDD8 and/or its transfer to a target protein, as well as compositions and methods for discovering molecules which are useful in detecting and/or modulating the conjugation of NEDD8 and/or its transfer to a target protein. The present invention arises from the purification and characterization of novel NEDD8 activating and conjugating enzymes.

The patents and publications cited herein reflect the knowledge in the art and are hereby incorporated by reference in entirety. Any inconsistency between these patents and publications and the present disclosure shall be resolved in favor of the present disclosure.

In a first aspect, the invention provides purified NEDD8-activating protein beta subunit (NAE1-beta). The primary amino acid sequence of a preferred embodiment of such NAE1-beta protein is shown in FIG. 1. However, the term "NEDD8-activating protein beta subunit", or "NAE1-beta", is intended to include allelic variants thereof. An "allelic variant", as used herein, is a protein having at least about 75% amino acid sequence, preferably at least about 85% more preferably at least about 95%, and most preferably at least about 99% identity to the amino acid sequence set forth in SEQ ID NO 2, or to a portion or protein conjugate thereof which retains the biological activity of NAE1-beta (as part of the NAE1 heterodimer) to form a thioester linkage with NEDD8 at a rate faster than the achieved by human ubiquitin activating enzyme 1, preferably at least 2-fold faster, more preferably at least 5-fold and most preferably at least 10-fold. Alternatively, an alleic variant can retain such biological activity and comprise a peptide sequence having at least 70% amino acid identity to the peptide sequence corresponding to residues 46–118 in FIG. 1, or at least 45% amino acid identity to the peptide sequence corresponding to residues 119–166, at least 55% amino acid identity to the peptide sequence corresponding to residues 175–239, or at least 35% amino acid identity to the peptide sequence corresponding to residues 276–375. Preferably such biologically active portion comprises at least the PXCT motif, wherein X can be any amino acid, preferably a hydrophobic amino acid, more preferably methionine, leucine, or isoleucine, and most preferably methionine. More preferably, such biologically active portion comprises amino acid sequence of residues 214–217, more preferably comprises at least about 25 additional amino acids of NAE1-beta, even more preferably at least about 50 additional amino acids of NAE1-beta, still more preferably at least about 75 additional amino acids of NAE1-beta, yet even more preferably at least about 100 additional amino acids of NAE1-beta, most preferably at least about 150 additional amino acids from NAE1-beta. Such allelic variants have the biological activity of NAE1-beta, as discussed above, which is the catalytic monomer of the NAE1 heterodimer. In alternative preferred embodiments, such allelic variants are either rationally designed or naturally occurring allelic variants, i.e., they are expressed in actual individual mammals, most preferably from actual individual humans or mice. Rationally designed allelic variants can be produced according to standard art-recognized procedures (e.g., international publication WO95/18974). "Purified", as used herein means having less than about 25% by weight, and preferably less than about 10% by weight contamination with other proteins. Such purified proteins may be obtained from natural sources, from recombinant expression, or by chemical synthesis. "Protein", as used herein and hereinbelow is intended to encompass any polypeptide having at least 10 amino acid residues.

In a second aspect, the invention provides NAE1-beta expression elements. Such elements include, without limitation, isolated or recombinant nucleic acid sequences encoding NAE1-beta or dominant negative mutants thereof, or capable of expressing antisense transcripts thereof or nucleic acid sequences specifically homologous or specifically complementary thereto, and vectors comprising any such recombinant expression elements, preferably expression vectors.

For purposes of the invention, amino acid sequence identity and homology are determined using the program Clustal W Version 1.6 to do sequence alignment (Thompson et al., Nucleic Acids Res 22: 4673–4680 (1994)). For viewing aligned sequences, the program GeneDoc Version 2.2 was used. A sequence is "specifically homologous" to another sequence if it is sufficiently homologous to specifically hybridize to the exact complement of the sequence. A sequence is "specifically complementary" to another sequence if it is sufficient homologous to specifically hybridize to the sequence. A sequence "specifically hybridizes" to another sequence if it hybridizes to form Watson-Crick or Hoogsteen base pairs either in the body, or under conditions which approximate physiological conditions with respect to ionic strength, e.g., 140 mM NaCl, 5 mM $MgCl_2$. Preferably, such specific hybridization is maintained under stringent conditions, e.g., 0.2× SSC at 68° C. A "recombinant expression element" is a nucleic acid sequence which encodes NAE1-beta, or a portion encoding at least 15 contiguous amino acids thereof, or a dominant negative mutant thereof, or is capable of expressing an antisense molecule specifically complementary thereto, or a sense molecule specifically homologous thereto wherein the recombinant expression unit may be in the form of linear DNA or RNA, covalently closed circular DNA or RNA, or as part of a chromosome, provided however that it cannot be the native chromosomal locus for NAE1-beta. Preferred recombinant expression elements are vectors, which may include an origin of replication and are thus replicable in or more cell type. Certain preferred recombinant expression elements are expression vectors, and further comprise at least a promoter and passive terminator, thereby allowing transcription of the recombinant expression element in a bacterial, fungal, plant, insect or mammalian cell. Preferred recombinant expression elements have at least 75% nucleic acid sequence identity with the nucleic acid sequence set forth in SEQ ID NO 1, more preferably at least 90%, even more preferably at least 95%, and most preferably at least 99%, and encode a protein or peptide having either NAE1-beta biological activity, as described above, or activity as a dominant negative mutant thereof, as further described below.

"Dominant negative mutants" are proteins derived from NAE1-beta or NAE1-alpha which inhibit the biological activity of NAE1. Preferred dominant negative mutants include allelic variants in which the C at position 216 is substituted, preferably by S. Additional preferred dominant negative mutants interfere with association of native NAE1-beta with native NAE1-alpha and can be derived from either NAE1-beta and NAE1-alpha. Such dominant negative mutants can be prepared by art recognized procedures (see e.g., Townsley et al., Proc. Natl. Acad. Sci. USA 94: 2362–2367 (1997)). Preferably, such dominant negative mutant is a protein or peptide having from 50% amino acid sequence identity to about 99% identity to the amino acid sequence set forth in SEQ ID NO 2, or to a portion or protein conjugate thereof which inhibits the biological activity of NAE1 to form a thioester linkage with NEDD8 or transfer NEDD8 to a NEDD8 conjugating enzyme, under conditions as described in the following examples by at least 50%, preferably by at least 75%, more preferably by at least 90% and most preferably by at least 99%. Preferably, such inhibitory portion comprises an amino acid sequence spanning residue 216, more preferably comprises at least about 25 additional amino acids of NAE1-beta, or at least about 50 additional amino acids of NAE1-beta, or at least about 75 additional amino acids of NAE1-beta, or at least about 100 additional amino acids of NAE1-beta, or even at least about 150 additional amino acids of NAE1-beta. For purposes of this aspect of the invention, the term "spanning residue 216" means comprising amino acid residues in both the N-terminal and C-terminal directions from residue 216, as that residue is shown in FIG. 1. Preferably, residue 216 itself may be substituted by one or more amino acids, more preferably from about 1 to about 50 amino acids, or residue 216 may be absent. Preferably the amino acids in the N-terminal and C-terminal directions from residue 216 are each independently within 20 amino acids of residue 216, as shown in FIG. 1, more preferably within 10, even more preferably within 5, and most preferably are immediately adjacent residue 216 as shown in FIG. 1.

The purified protein and its structural information provided herein enables the preparation of NAE1-beta-binding molecules (NAE1BBMs). Thus, in a third aspect, the invention provides methods for identifying NAE1BBMs. One preferred method according to this aspect of the invention comprises screening for NAE1BBMs by contacting purified NAE1-beta according to the invention and populations of molecules or mixed populations of molecules and determining the presence of molecules which bind specifically to NAE1-beta. Another preferred method according to this aspect of the invention comprises rationally designing molecules to bind NAE1-beta based upon structural information from the purified NAE1-beta protein and amino acid sequence disclosed herein provided by the invention and determining whether such rationally designed molecules bind specifically to NAE1-beta. Molecules that bind specifically to NAE1-beta are molecules that bind to NAE1-beta with greater affinity than to other unrelated proteins. Preferably, binding affinity of the molecule is at least 5-fold greater than affinity for unrelated proteins, more preferably at least 10-fold greater, still more preferably at least 50-fold greater, and most preferably at least 100-fold greater. This aspect of the invention includes NAE1BBMs identified by the methods according to the invention.

As used herein, a "NAE1-beta-binding molecule", or "NAE1BBM", is a molecule or macromolecule which binds under physiological conditions to NAE1-beta. "Binds under physiological conditions" means forming a covalent or non-covalent association with an affinity of at least $10^6$ $M^{-1}$, most preferably at least $10^9$ $M^{-1}$, either in the body, or under conditions which approximate physiological conditions with respect to ionic strength, e.g., 140 mM NaCl, 5 mM $MgCl_2$. A "population of molecules", as used herein, refers to a plurality of identical molecules. A "mixed population of molecules" refers to a plurality of molecules wherein more than one type of molecule is present.

In certain preferred embodiments, an NAE1BBM according to the invention is a peptide or a peptidomimetic. For purposes of the invention, a "peptide" is a molecule comprised of a linear array of amino acid residues connected to each other in the linear array by peptide bonds. Such peptides according to the invention may include from about three to about 500 amino acids, and may further include secondary, tertiary or quaternary structures, as well as intermolecular associations with other peptides or other non-peptide molecules. Such intermolecular associations may be through, without limitation, covalent bonding (e.g., through disulfide linkages), or through chelation, electrostatic interactions, hydrophobic interactions, hydrogen bonding, ion-dipole interactions, dipole—dipole interactions, or any combination of the above.

In certain preferred embodiments, such an NAE1BBM comprises a complementarity determining region of an antibody which binds under physiological conditions to a peptide-containing epitope of NAE1-beta, or a peptidomimetic of such a complementarity determining region. For purposes of the invention, a "complementary determining region of an antibody" is that portion of an antibody which binds under physiological conditions to an epitope, including any framework regions necessary for such binding, and which is preferably comprised of a subset of amino acid residues encoded by the human heavy chain V, D and J regions, the human light chain V and J regions, and/or combinations thereof. Examples of such preferred embodiments include an antibody, or an antibody derivative, which may more preferably be a monoclonal antibody, a human antibody, a humanized antibody, a single-chain antibody, a chimeric antibody, or an antigen-binding antibody fragment.

Those skilled in the art are enabled to make any such antibody derivatives using standard art-recognized techniques. For example, Jones et al., Nature 321: 522–525 (1986) discloses replacing the CDRs of a human antibody with those from a mouse antibody. Marx, Science 229: 455–456 (1985) discusses chimeric antibodies having mouse variable regions and human constant regions. Rodwell, Nature 342: 99–100 (1989) discusses lower molecular weight recognition elements derived from antibody CDR information. Clackson, Br. J. Rheumatol. 3052: 36–39 (1991) discusses genetically engineered monoclonal antibodies, including Fv fragment derivatives single chain antibodies, fusion proteins chimeric antibodies and humanized rodent antibodies. Reichman et al., Nature 332: 323–327 (1988) discloses a human antibody on which rat hypervariable regions have been grafted. Verhoeyen, et al., Science 239: 1534–1536 (1988) teaches grafting of a mouse antigen binding site onto a human antibody.

In addition, those skilled in the art are enabled to design and produce peptidomimetics having binding characteristics similar or superior to such complementarity determining region (see e.g., Horwell et al., Bioorg. Med. Chem. 4: 1573 (1996); Liskamp et al., Recl. Trav. Chim. Pays- Bas1: 113 (1994); Gante et al., Angew. Chem. Int. Ed. Engl. 33: 1699 (1994); Seebach et al., Helv. Chim. Acta 79: 913 (1996)). Accordingly, all such antibody derivatives and peptidomimetics thereof are contemplated to be within the scope of the present invention. Compositions according to the invention may further include physiologically acceptable diluents, stabilizing agents, localizing agents or buffers.

Additional preferred NAE1BBMs according to the invention include small molecules, which can be identified using screening or rational design approaches as discussed later herein.

NAE1BBMs can be used in conventional assays to detect the presence or absence, and or quantity of NAE1-beta, NAE1 heterodimer, or NAE1 heterodimer/NEDD8 complex in a biological sample. Thus, in a fourth aspect, the invention provides methods for determining the presence or absence and/or quantity of NAE1-beta, NAE1 heterodimer, or NAE1 heterodimer/NEDD8 complex in a biological sample. Such methods comprise providing a detectable NAE1BBM to a biological sample, allowing the detectable NAE1BBM to bind to NAE1-beta, NAE1 heterodimer, or NAE1 heterodimer/NEDD8 complex, if any is presen in the biological sample, and detecting the presence or absence/or quantity of a complex of the detectable NAE1BBM and NAE1-beta, NAE1-heterodimer, or NAE1 heterodimer/NEDD8 complex.

A detectable NAE1BBM is an NAE1BBM which can be detected in an assay. Such detection is preferably through the direct or indirect binding of a tag or label on the NAE1BBM. "Direct or indirect binding" means that the tag or label may be directly connected to the NAE1BBM by intermolecular association, or may be connected via intermediate molecules to the NAE1BBM by intermolecular association. Such intermolecular associations may be through, without limitation, covalent bonding (e.g., through disulfide linkages), or through chelation, electrostatic interactions, hydrophobic interactions, hydrogen bonding, ion-dipole interactions, dipole—dipole interactions, or any combination of the above. Preferred tags and labels include, without limitation, radioisotopes, heavy metals, fluorescent labels, chemoluminescent labels, enzymes and enzyme substrates. Preferred biological samples include blood, serum, plasma, cells, tissue portions, and cell or tissue extracts. In certain preferred embodiments, the method according to this aspect of the invention takes the form of a conventional ELISA or RIA. In another preferred embodiment, the method employs either direct or indirect immunofluorescence. Additional preferred embodiments utilize in vivo imaging of cells expressing NAE1-beta using conventional imaging agents directly or indirectly bound to an NAE1BBM according to the invention.

Nucleic acid sequences specifically complementary to and/or specifically homologous to nucleic acid sequences encoding NAE1-beta can also be used in conventional assays to detect the presence or absence of NAE1-beta nucleic acid in a biological sample. Thus, in a fifth aspect, the invention provides methods for determining the presence or absence and/or quantity of NAE1-beta nucleic acid in a biological sample. In preferred embodiments, such assays are nucleic acid hybridization and/or amplification assays, such assays comprising providing to the biological sample a nucleic acid sequence which is specifically complementary to NAE1-beta nucleic acid. Particularly, preferred embodiments include Northern blotting, dot or slot blotting, and polymerase chain reaction.

In a sixth aspect, the invention provides methods for identifying modulating ligands of NAE1-beta. Some NAE1BBMs are capable of acting as antagonists or agonists of NAE1-beta. Thus, the method according to this aspect of the invention comprises providing NAE1BBMs to an assay system for NAE1-beta participation in the NEDD8-activation/conjugation pathway, and determining whether such NAE1BBMS interfere with or enhance the ability of NAE1-beta to participate in the NEED8-activation/conjugation pathway. The NAE1BBMs are preferably provided as a population of molecules (most preferably rationally designed molecules), or as a mixed population of molecules, as for example in a screening procedure. This aspect of the invention includes antagonists or agonists of NAE1-beta identified by this method according to the invention. Assessment of ability to "interfere with or enhance the ability to participate in the NEDD8-activation/conjugation pathway" can conveniently be carried out using an in vitro activity system, as later described herein. Preferably, such interference or enhancement results in a reduction of NEDD8 activation/conjugation of at least 50%, more preferably at least 90%, and most preferably, at least 99%, or an increase of NEDD8 activation/conjugation of at least 50%, preferably at least 2-fold, the preferably at least 5-fold.

In a seventh aspect, the invention provides modulating ligands of NAE1-beta. Preferred modulating ligands are NAE1BBMs which act as antagonists, interfering with the ability of NAE1-beta to participate in the NEDD8-activation/conjugation pathway. Other preferred modulating ligands are NAE1BBMs which act as agonists, enhancing the ability of NAE1-beta to participate in the NEDD8-activation/conjugation pathway. Preferably, such inhibition or enhancement is specific, i.e., the modulating ligand interferes with or enhances the ability of NAE1-beta to participate in the NEDDS activation/conjugation pathway at a concentration that is lower than the concentration of the ligand required to produce another, unrelated biological effect. Preferably, the concentration of the ligand required for NEDD8 activation/conjugation modulating activity is at least 2-fold lower, more preferably at least 5-fold lower, even more preferably at least 10-fold lower, and most preferably at least 20-fold lower than the concentration required to produce an unrelated biological effect. In certain embodiments, such NAE1BBMs preferably interact with NAE1-beta to inhibit or enhance the formation of NAE1 heterodimer, the formation of NEDD8 adenylate, the formation of a thiol ester bond between NEDD8 and NAE1, and/or transfer of NEDD8 to NEDD8-conjugating enzyme.

In an eighth aspect, the invention provides methods for modulating the conjugation of NEDD8 to NAE1 or its transfer to a NEDD8 conjugating enzyme or a target protein. One preferred embodiment of the method according to this aspect of the invention comprises providing a modulating ligand of NAE1-beta or a recombinant expression unit which expresses NAE1-beta or an antagonist thereof to a biological system in which NEDD8 is conjugated to a NEDDS conjugating enzyme or a target protein.

The term "biological system", as used herein, includes in vitro cell or tissue extracts, cell cultures, tissue cultures, organ cultures, living plants and animals, including mammals, including without limitation humans and mice. An "antagonist" is a molecule which inhibits the biological activity of NAE1.

In a ninth aspect, the invention provides oligonucleotides that are specifically complementary to a portion of a nucleotide sequence shown in FIG. 1. Preferred embodiments include hybridization probes and antisense oligonucleotides.

For purposes of the invention, the term oligonucleotide includes polymers of two or more deoxyribonucleotide, or any modified nucleoside, including 2'-halo-nucleosides, 2'-O-substituted ribonucleosides, deazanucleosides or any combination thereof. Preferably, such oligonucleotides have from about 10 to about 100 nucleosides, more preferably from about 15–50, and most preferably from about 15 to 35. Such monomers may be coupled to each other by any of the numerous known internucleoside linkages. In certain preferred embodiments, these internucleoside linkages may be phosphodiester, phosphotriester, phosphorothioate, or phosphoramidate linkages, or combinations thereof. The term oligonucleotide also encompasses such polymers having chemically modified bases or sugars and/or having additional substituents, including without limitation lipophilic groups, intercalating agents, diamines and adamantane. For purposes of the invention the term "2'-O-substituted" means substitution of the 2' position of the pentose moiety with a halogen (preferably Cl, Br, or F), or an O-lower alkyl group containing 1–6 saturated or unsaturated carbon atoms, or with an O-aryl or allyl group having 2–6 carbon atoms, wherein such alkyl, aryl or allyl group may be unsubstituted or may be substituted, e.g., with halo, hydroxy, trifluoromethyl, cyano, nitro, acyl, acyloxy, alkoxy, carboxyl, carbalkoxyl, or amino groups, or such 2' substitution may be with a hydroxy group (to produce a ribonucleoside), an amino or a halo group, but not with a 2'-H group. Certain embodiments of such oligonucleotides are useful in hybridization assays. Other embodiments are useful as antisense oligonucleotides for use in animal model or human therapeutic settings.

In a tenth aspect, the invention provides methods for identifying NAE1-alpha binding molecules (NAE1ABMs). The present inventors have identified the alpha subunit of the NAE1 heterodimer (NAE1-alpha). Surprisingly, it has an amino acid sequence which is substantially identical to a protein previously identified as amyloid precursor protein binding protein 1 (APP-BP1; see Chow et al. J. Biol. Chem. 271: 11339–11346 (1996)) One preferred method according to this aspect of the invention comprises screening for NAE1ABMs by contacting purified NAE1-alpha and populations of molecules or mixed populations of molecules and determining the presence of molecules which bind specifically to NAE1-alpha, or preferably to NAE1 heterodimer. Another preferred method according to this aspect of the invention comprises rationally designing molecules to bind NAE1-alpha based upon structural information from the NEA1-alpha protein identified by the present inventors and determining whether such rationally designed molecules bind specifically to NAE1-alpha. This aspect of the invention includes NAE1ABMs identified by the methods according to the invention.

The terms "bind specifically", "population of molecules" and "mixed population of molecules" are as described previously. Structural aspects of NAE1ABMs are as discussed above for NAE1BBMs, except that NAE1ABMs bind under physiological conditions to NAE1-alpha. Preferably, binding affinity of the molecule for NAE1-alpha is at least 5-fold greater than affinity for unrelated proteins, more preferably at least 10-fold greater, still more preferably at least 50-fold greater, and most preferably at least 100-fold greater. This aspect of the invention includes NAE1ABMs identified by the methods according to the invention.

As used herein, a "NAE1-alpha-binding molecule", or "NAE1ABM", is a molecule or macromolecule which binds under physiological conditions to NAE1-alpha. The terms "binds under physiological conditions", "population of molecules", and "mixed population of molecules" are as used previously.

In certain preferred embodiments, an NAE1ABM according to the invention is a peptide or a peptidomimetic. For purposes of the invention, the term "peptide" is as used previously.

In certain preferred embodiments, such an NAE1ABM comprises a complementarity determining region of an antibody which binds under physiological conditions to a peptide-containing epitope of NAE1-alpha, or a peptidomimetic of such a complementarity determining region. For purposes of the invention, the term "complementarity determining region of an antibody" is as used previously. Compositions according to the invention may further include physiologically acceptable diluents, stabilizing agents, localizing agents or buffers.

Additional preferred NAE1ABMs according to the invention include small molecules, which can be identified using screening or rational design approaches as discussed later herein.

NAE1ABMs can be used in conventionally assays to detect the pressure or absence, and/or quantity of NAE1-alpha, NAE1 heterodimer, or NAE1 heterodimer/NEDD8 complex in a biological sample. Thus, in an eleventh aspect, the invention provides methods for determining the presence or absence and/or quantity of NAE1-alpha, NAE1 heterodimer, or NAE1 heterodimer/NEDD8 complex in a biological sample. Such methods comprise providing a detectable NAE1ABM to a biological sample, allowing the detectable NAE1ABM to bind to NAE1-alpha, NAE1 heterodimer, or NAE1 heterodimer/NEDD8 complex, if any is present in the biological sample, and detecting the presence or absence and/or quantity of a complex of the detectable NAE1ABM and NAE1-alpha, NAE1-heterodimer, or NAE1 heterodimer/NEDD8 complex.

A detectable NAE1ABM is an NAE1ABM which can be detected in an assay. Such detection is preferably through the direct or indirect binding of a tag or label on the NAE1ABM. The term "direct or indirect binding" is as used previously. Preferred tags and labels include, without limitation, radioisotopes, heavy metals, fluorescent labels, chemoluminescent labels, enzymes and enzyme substrates. Preferred biological samples include blood, serum, plasma, cells, tissue portions, and cell or tissue extracts. In certain preferred embodiments, the method according to this aspect of the invention takes the form of a conventional ELISA or RIA. In another preferred embodiment, the method employs either direct or indirect immunofluorescence. Additional preferred embodiments utilize in vivo imaging of cells expressing NAE1-alpha using conventional imaging agents directly or indirectly bound to an NAE1ABM according to the invention.

Nucleic acid sequences specifically complementary to and/or specifically homologous to nucleic acid sequences encoding NAE1-alpha can also be used in conventional assays to detect the presence or absence of NAE1-alpha nucleic acid in a biological sample. Thus, in a twelfth aspect, the invention provides methods for determining the presence or absence and/or quantity of NAE1-alpha nucleic acid in a biological sample. In preferred embodiments, such assays are nucleic acid hybridization and/or amplification assays, such assays comprising providing to the biological sample a nucleic acid sequence which is specifically complementary to NAE1-alpha nucleic acid. Particularly preferred embodiments include Northern blotting, dot or slot blotting, and polymerase chain reaction.

In a thirteenth aspect, the invention provides methods for identifying modulating ligands of NAE1-alpha. Some NAE1ABMs are capable of acting as antagonists or agonists of NAE1-alpha. Thus, the method according to this aspect of the invention comprises providing NAE1ABMs to an assay system for NAE1-alpha participation in the NEDD8-activation/conjugation pathway, and determining whether such NAE1ABMs interfere with or enhance the ability of NAE1-alpha to participate in the NEDD8-activation/conjugation pathway. The NAE1ABMs are preferably provided as a population of molecules (most preferably rationally designed molecules), or as a mixed population of molecules, as for example in a screening procedure. This aspect of the invention includes antagonists or agonists of NAE1-alpha identified by this method according to the invention. Assessment of ability to "interfere with or enhance the ability to participate in the NEDD8-activation/conjugation pathway" can conventionally be carried out using an in vitro activity system, as later described herein. Preferably, such interference or enhancement results in a reduction of NEDD8 activation/conjugation of at least 50%, more preferably at least 90%, and most preferably, at least 99%, or an increase of NEDD8 activation/conjugation of at least 50%, preferably at least 2-fold, more preferably at least 5-fold.

In a fourteenth aspect the invention provides a purified complex of NAE1-beta and NAE1-alpha, or NAE1-beta, NAE1-alpha and NEDD8, or a purified complex of portions thereof. The term "complex" means in covalent or noncovalent association, preferably with an affinity greater than $10^6$/mole. The term "purified" is as used previously.

In a fifteenth aspect, the invention provides modulating ligands of NAE1-alpha. Preferred modulating ligands as NAE1ABMs which act as antagonists, interfering with the ability of NAE1-alpha to participate in the NEDD8-activation/conjugation pathway. Other preferred modulating ligands are NAE1ABMs which act as agonists, enhancing the ability of NAE1-alpha to participate in the NEDD8-activation/conjugation pathway. Preferably, such inhibition or enhancement is specific, i.e., the modulating ligand interferes with or enhances the ability of NAE1-alpha to participate in the NEDD8 activation/conjugation pathway at a concentration that is lower than the concentration of the ligand required to produce another, unrelated biological effect. Preferably, the concentration of the ligand required for NEDD8 activation/conjugation modulating activity is at least 2-fold lower, more preferably at least 5-fold lower, even more preferably at least 10-fold lower, and most preferably at least 20-fold lower than the concentration required to produce an unrelated biological effect. In certain embodiments, such NAE1ABMs preferably interact with NAE1-alpha to inhibit or enhance the formation of NAE1 heterodimer, the formation of NEDD8 adenylate, the formation of a thiol ester bond between NEDD8 and NAE1, and/or transfer of NEDD8 to NEDD8-conjugating enzyme.

In a sixteenth aspect, the invention provides methods for modulating the conjugation of NEDD8 to NAE1 or its transfer to a NEDD8 conjugating enzyme or a target protein. One preferred embodiment of the method according to this aspect of the invention comprises providing a modulating ligand of NAE1-alpha or a recombinant expression unit which expresses NAE1-alpha or an antogonist thereof to a biological system in which NEDD8 is conjugated to a NEDD8 conjugating enzyme or a target protein.

The term "biological system", as used herein, includes in vitro cell or tissue extracts, cell cultures, tissue cultures, organ cultures, living plants and animals, including mammals, including without limitation humans and mice. An "antagonist" is a molecule which inhibits the biological activity of NAE1.

In a seventeenth aspect, the invention provides allelic variants of NAE-1 alpha. An "allelic variant", as used herein, is a protein having at least about 75% amino acid sequence, preferably at least about 85%, more preferably at least about 95%, and most preferably at least about 99% identity to the amino acid sequence of NAE1-alpha, or to a portion or protein conjugate thereof which retains the biological activity of NAE1-alpha to form a heterodimer with NAE1-beta which is active in the NEDD8 activation/conjugation pathway. This aspect of the invention further includes NAE1-alpha allelic variant expression elements. Such elements include, without limitation, isolated or recombinant nucleic acid sequences encoding NAE1-alpha, or nucleic acid sequences specifically homologous or specifically complementary thereto, vectors comprising any such nucleic acid sequences, and recombinant expression units which express NAE1-beta or antisense transcripts or dominant negative mutants thereof. Each of these terms is as used previously.

In a eighteenth aspect, the invention provides methods for modulating auxin response in plants. The present inventors have discovered that NAE1-alpha shares 39% identity and 61% conserved residues with Aux1 in *A. Thaliana,* which is involved in signal transduction in the auxin respone in plants. This suggests that antagonists of NAE1-beta and/or NAE1-alpha should down-regulate the auxin response, and that expression of NAE1beta and/or NAE1-alpha should up-regulate the auxin response (see Leyser et al., Nature 364: 161–164 (1993)). One preferred embodiment of the method according to this aspect of the invention comprises providing a modulating ligand of NAE1-beta or NAE1-alpha or a recombinant expression unit which expresses NAE1-beta or NAE1 or an antagonist thereof to a plant that is undergoing auxin treatment.

In a nineteenth aspect, the invention provides methods for modulating the biological function of APP and/or beta peptide accumulation in a biological system. The present inventors have discovered that NAE1-alpha is substantially the same protein as amyloid precursor protein binding protein-1 (APP-BP1). This suggests that antagonists or agonists of NAE1-beta and/or NAE1-alpha should modulate APP function, including its role in beta peptide accumulation. One preferred embodiment of the method according to this aspect of the invention comprises providing a modulating ligand of NAE1-beta or NAE1-alpha or a recombinant expression unit which expresses NAE1-beta or NAE1 or an antagonist thereof to a biological system.

In a twentieth aspect, the invention provides two new purified NEDD8-conjugating enzymes. The primary amino acid sequence of a preferred embodiment of a first such NEDD8-conjugating enzyme (NCE1) is shown in FIG. 2. The primary amino acid sequence of a preferred embodiment of a second such NEDD8-conjugating enzyme (NCE2) is shown in FIG. 5. However, the terms "NEDD8-conjugating enzyme 1", "NCE1", "NEDD8-conjugating enzyme 2", and "NCE2" are intended to include allelic variants thereof. An "allelic variant", are used herein, is a protein having at least about 50% amino acid sequence identity, more preferably at least about 75%, even more preferably at least about 85%, still more preferably at least about 95%, and most preferably at least about 99% identity to the amino acid sequence set forth in SEQ ID NO 4 or SEQ ID NO 6, or to a portion or protein conjugate thereof which retains the biological activity of NCE1 or NCE2 to form a thioester linkage with NEDD8 under conditions as described in the examples below at a rate least 10% of that of NCE1 or NCE2, preferably at least 25% as fast, more preferably at least 50% as fast, and most preferably at least 75% as fast. Preferably, such biologically active portion comprises an amino acid sequence spanning residue 111 in FIG. 2 or residue 116 in FIG. 5, more preferably comprises at least about 25 additional amino acids of respectively NCE1 or NCE2, even more preferably at least about 50 additional amino acids of respectively NCE1 or NCE2, still more preferably at least about 75 additional amino acids of respectively NCE1 or NCE2, yet even more preferably at least about 100 additional amino acids of respectively NCE1 or NCE2, most preferably at least about 150 additional amino acids from respectively NCE1 or NCE2. Such allelic variants have the biological activity of NCE1 or NCE2, as discussed above. In alternative preferred embodiments, such allelic variants are either rationally designed or naturally occurring allelic variants, i.e., they are expressed in actual individual mammals, most preferably from actual individual humans or mice. Rationally designed allelic variants can be produced according to standard art-recognized procedures (see e.g., international publication WO95/18974). The terms "purified" and "protein" are as used previously.

In a twenty-first aspect, the invention provides NEDD8-conjugation enzyme expression elements. Such elements include, without limitation, isolated or recombinant nucleic acid sequences encoding NCE1 or NCE2 or dominant negative mutants thereof, or capable of expressing antisense transcripts thereof or nucleic acid sequences specifically homologous or specifically complementary thereto, and vectors comprising any such recombinant expression elements, preferably expression vectors.

The terms "specifically homologous", "specifically complementary" and "specifically hybridizes" are as used previously. A "recombinant expression element" is a nucleic acid sequence which encodes NCE1 or NCE2, or a portion encoding at least 20 contiguous amino acids thereof, or a dominant negative mutant thereof, or is capable of expressing an antisense molecule specifically complementary thereto, or a sense molecule specifically homologous thereto wherein the recombinant expression unit may be in the form of linear DNA or RNA, covalently closed circular DNA or RNA, or as part of a chromosome, provided however that it cannot be the native chromosomal locus for NCE1 or NCE2. Preferred recombinant expression elements are vectors, which may include an origin of replication and are thus replicatable in one or more cell type. Certain preferred recombinant expression elements are expression vectors, and further comprise at least a promoter and passive terminator, thereby allowing transcription of the recombinant expression element in a bacterial, fungal, plant, insect or mammalian cell. Preferred recombinant expression elements have at least 75% nucleic acid sequence identity with the nucleic acid sequence set forth in SEQ ID NO 2 OR SEQ ID NO 4, more preferably at least 90%, even more preferably at least 95%, and most preferably at least 99%, and encode a protein or peptide having either NCE1 or NCE2 biological activity or activity as a dominant negative mutant thereof, as further described below.

"Dominant negative mutants" are proteins or peptides derived from NCE1 or NCE2 which inhibit the biological activity of, respectively NCE1 or NCE2. Preferred dominant negative mutants include variants in which the C at position 111 of NCE1 or position 116 of NCE2 is substituted, preferably by S. Preferred dominant negative mutants interfere with association of NEDD8 and NCE1 or NCE2 and can be derived from respectively, NCE1 or NCE2. Other preferred dominant negative mutants interfere with conjugation of NEDD8 to a target protein and can be derived from either NCE1 or NCE2. Such dominant negative mutants can be prepared by art recognized procedures (see e.g., Townsley et al., Proc. Natl. Acad. Sci. USA 94: 2362–2367 (1997)). Preferably, such dominant negative mutant is a protein or peptide having from 50% amino acid sequence identity to about 99% identity to the amino acid sequence set forth in SEQ ID NO 3 or SEQ ID NO 5, or to a portion or protein conjugate thereof which inhibits the biological activity of NCE1 or NCE2 to form a thioester linkage with NEDD8 under conditions as described in the following examples by at least 50%, preferably by at least 75%, more preferably by at least 90% and most preferably by at least 99%. Preferably, such inhibitory portion comprises an amino acid sequence spanning residue 111 in FIG. 2 or residue 116 in FIG. 5, more preferably comprises at least about 25 additional amino acids of respectively NCE1 or NCE2, even more preferably at least about 50 additional amino acids of respectively NCE1 or NCE2, still more preferably at least about 75 additional amino acids of respectively NCE1 or NCE2, yet even more preferably at least about 100 additional amino acids of respectively NCE1 or NCE2, most preferably at least about 150 additional amino acids from respectively NCE1 or NCE2.

The purified protein and its structural information provided herein enables the preparation of NCE1 and NCE2 binding molecules, respectively NCE1BMs and NCE2BMs. Thus, in a twenty second aspect, the invention provides methods for identifying NCE1BMs and NCE2BMs. One preferred method according to this aspect of the invention comprises screening for NCE1BMs or NCE2BMs by contacting purified NCE1 or NCE2 according to the invention and populations or molecules or mixed populations of molecules and determining the presence of molecules which bind specifically to NCE1 or NCE2. Another preferred method according to this aspect of the invention comprises rationally designing molecules to bind NCE1 or NCE2 based upon structural information from the purified NCE1 or NCE2 provided by the invention and determining whether such rationally designed molecules bind specifically to NCE1 or NCE2. Molecules that bind specifically to NCE1 or NCE2 are molecules that bind to NCE1 or NCE2 with greater affinity than to other unrelated proteins. Preferably, binding affinity of the molecule is at least 5-fold greater than affinity for unrelated proteins, more preferably at least 10-fold greater, still more preferably at least 50-fold greater, and most preferably at least 100-fold greater. This aspect of the invention includes NCE1BMs or NCE2BMs identified by the methods according to the invention.

As used herein, a "NCE1 or NCE2-binding molecule", or "NCE1BM or NCE2BM", is a molecule or macromolecule which binds under physiological conditions to, respectively NCE1 or NCE2. The terms "binds under physiological conditions", "population of molecules" and "mixed population of molecules" are as used previously.

In certain preferred embodiments, an NCE1BM or NCE2BM according to the invention is a peptide or a peptidomimetic. For purposes of the invention, the term "peptide" is as used previously.

In certain preferred embodiments, such as NCE1BM or NCE2BM comprises a complementarity determining region of an antibody which binds under physiological conditions to a peptide-containing epitope of, respectively NCE1 or NCE2, or a peptidomimetic of such a complementarity determining region. For purposes of the invention, the term "complementarity determining region of an antibody" is as used previously. Accordingly, all such antibody derivatives and peptidomimetics thereof are contemplated to be within the scope of the present invention. Compositions according to the invention may further include physiologically acceptable diluents, stabilizing agents, localizing agents or buffers.

Additional preferred NCE1BMs and NCE2BMs according to the invention include small molecules, which can be identified using screening or rational design approaches as discussed later herein.

NCE1BMs and NCE2BMs can be used in conventional assays to detect the presence or absence, and/or quantity of NCE1, or NCE2, or NCE1 or NCE2/NEDD8 complex in a biological sample. Thus, in a twenty-third aspect, the invention provides methods of determining the presence or absence and/or quantity of NCE1 or NCE2, or NCE1 or NCE2/NEDD8 complex in a biological sample. Such methods comprise providing a detectable NCE1BM or NCE2BM to a biological sample, allowing the detectable NCE1BM or NCE2BM to bind to NCE1, or NCE1 or NCE2/NEDD8 complex, if any is present in the biological sample, and detecting the presence or absence and/or quantity of a complex of the detectable NCE1BM or NCE2BM and, respectively, NCE1 or NCE2, or NCE1 or NCE2/NEDD8 complex.

A detectable NCE1BM or NCE2BM is an NCE1BM or NCE2BM which can be detected in an assay. Such detection is preferably through the direct or indirect binding of a tag or label on the NCE1BM or NCE2BM. The term "direct or indirect binding" is as used previously. Preferred tags and labels include, without limitation, radiostopes, heavy metals, fluorescent labels, chemoluminescent labels, enzymes and enzyme substrates. Preferred biological samples include blood, serum, plasma, cells, tissue portions, and cell or tissue extracts. In certain preferred embodiments, the method according to this aspect of the invention takes the form of a conventional ELISA or RIA. In another preferred embodiment, the method employs either direct or indirect immunofluorescence. Additional preferred embodiments utilize in vivo imaging of cells expressing NCE1 or NCE2 using conventional imaging agents directly or indirectly bound to an NCE1BM or NCE2BM according to the invention.

Nucleic acid sequences specifically complementary to and/or specifically homologous to nucleic acid sequences encoding NCE1 or NCE2 can also be used in conventional assays to detect the presence or absence of NCE1 or NCE2 nucleic acid in a biological sample. Thus, in a twenty-fourth aspect, the invention provides methods for determining the presence or absence and/or quantity of NCE1 or NCE2 nucleic acid in a biological sample. In preferred embodiments, such assays are nucleic acid hybridization and/or amplification assays, such assays comprising providing to the biological sample a nucleic acid sequence which is specifically complementary to NCE1 to NCE2 nucleic acid. Particularly preferred embodiments include Northern blotting, dot or slot blotting, and polymerase chain reaction.

In a twenty-fifth aspect, the invention provides methods for identifying modulating ligands of NCE1 or NCE2. Some NCE1BMs and NCE2BMs are capable of acting as antagonists or agonists of, respectively, NCE1 and NCE2. Thus, the method according to this aspect of the invention comprises providing NCE1BMs or NCE2BMs to an assay system for, respectively, NCE1 or NCE2 participation in the NEDD8-activation/conjugation pathway, and determining whether such NCE1BMs or NCE2BMs interfere with or enhance the ability of NCE1 or NCE2 to participate in the NEDD8-activation/conjugation pathway. The NCE1BMS or NCE2BMs are preferably provided as a population of molecules (most preferably rationally designed molecules), or as a mixed population of molecules, as for example in a screening procedure. This aspect of the invention includes antagonists or agonists of NCE1 or NCE2 identified by this method according to the invention. Assessment of ability to "interfere with or enhance the ability to participate in the NEDD8-activation/conjugation pathway" can conveniently be carried out using an in vitro activity system, as later described herein. Preferably, such interference or enhancement results in a reduction of NEDD8 activation/conjugation of at least 50%, more preferably at least 90%, and most preferably, at least 99%, or an increase of NEDD8 activation/conjugation of at least 50%, preferably at least 2-fold, more preferably at least 5-fold, most preferably at least 10-fold.

In a twenty-sixth aspect, the invention provides modulating ligands of NCE1 or NCE2. Preferred modulating ligands are NCE1BMs or NCE2BMs which act as antagonists, interfering with the ability of, respectively, NCE1 or NCE2 to participate in the NEDD8-activation/conjugation pathway. Other preferred modulating ligands are NCE1BMs or NCE2BMs which act as agonists, enhancing the ability of, respectively NCE1 or NCE2 to participate in the NEDD8-activation/conjugation pathway. Preferably, such inhibition or enhancement is specific, i.e., the modulating ligand interferes with or enhances the ability of NCE1 or NCE2 to participate in the NEDD8 activation/conjugation pathway at a concentration that is lower than the concentration of the ligand required to produce another, unrelated biological effect. Preferably, the concentration of the ligand required for NEDD8 activation/conjugation modulating activity is at least 2-fold lower, more preferably at least 5-fold lower, even more preferably at least 10-fold lower, and most preferably at least 20-fold lower than the concentration required to produce an unrelated biological effect. In certain embodiments, such NCE1BMs or NCE2BMs preferably interact with, respectively, NCE1 or NCE2 to inhibit or enhance the formation of a thiol ester bond between NEDD8 and NCE1 or NCE2, and/or transfer of NEDD8 to a target protein.

In a twenty-seventh aspect, the invention provides methods for modulating the formation of a thiol ester bond between NEDD8 and NCE1 or NCE2, or transfer of NEDD8 to a target protein. One preferred embodiment of the method according to this aspect of the invention comprises providing a modulating ligand of NCE1 or NCE2 or a recombinant expression unit which expresses NCE1 or NCE2 or an antagonist thereof to a biological system in which NEDD8 is conjugated to another protein. The term "biological system", as used herein, includes in vitro cell or tissue extracts, cell cultures, tissue cultures, organ cultures, living plants and animals, including mammals, including without limitation humans and mice.

In twenty-eighth aspect, the invention provides oligonucleotides that are specifically complementary to a portion of a nucleotide sequence shown in FIG. 2 or FIG. 5. For purposes of the invention, the term "oligonucleotide" is as used previously. Certain embodiments of such oligonucleotides are useful as antisense probes. Other embodiments are useful as antisense oligonucleotides for use in animal model or human therapeutic settings.

In a twenty-ninth aspect the invention provides a purified complex of NCE1 and NEDD8, or of NCE2 and NEDD8. The terms "complex" and "purified" are as used previously.

The following examples are intended to further illustrate certain particularly preferred embodiments of the invention and are not intended to limit the scope of the invention. Searches of the human EST database utilized the program BLAST (Altschul et al., Nucleic Acid Res 25: 3389–3402 (1997)). Searches for transmembrane helices used the program Antheprot V.3.0 Gilbert Deleague, Institute de Biologie et Chemie des Proteines 69 367 Lyon cdex 07, France.

EXAMPLE 1

Preparation of Human NEDD8

Nucleotide sequence coding the N-terminal 76 residues of human Nedd8 was obtained from a human leukocyte cDNA Library (Life Technologies Tech-Line$^{SM}$, Inc) by nested polymerase chain reaction, using 5'-ccg tgt gca gcc cca aac tgg and 5'-aca ggg taa aga ggt aaa atg as the first round forward and reverse primer, respectively. In the second round, 5'-ggg aat tcc ata tgc taa tta aag tga aga cgc and 5'-cc aag ctt tca tcc tcc tct cag agc caa cac were used as the forward and reverse primer, respectively. The second PCR product was digested with Nde1 and HindIII and ligated to the large fragment of a similarly digested PT7-7 vector. The construct was transformed into the E. coli strain BL21 (DE3)/pLysS (Novagen). Nedd8 expression was induced by the addition of 0.5 mM IPTG. The S100 fraction of bacterial extracts was applied to a Q-Sepharose column in 50 mM HEPES, pH 7.5 and the flow-through which contained Nedd8 was collected, concentrated by ultrafiltration and fractionated by size exclusion chromatography on Superdex G75.

EXAMPLE 2

Identification of NEDD8-Activating Enzyme

To identify the human Nedd8-activating enzyme, we first tested for the presence of this enzyme activity by monitoring the incorporation of Nedd8 in the form of a thioester linkage into proteins derived from Hela cells. On the basis of the chromatographic behavior of recombinant human Nedd8, we generated from Hela cell extracts two protein fractions (FI and FII) which are expected to be devoid of endogenous Nedd8 as follows. To remove Nedd8, 400 mg of protein from Hela cell S100 fraction was applied to a 70 ml Q-Sepharose column, equilibrated with 50 mM HEPES, pH 8.0 with 1 mM DTT. Proteins in the flow-through fraction were precipitated in 90% ammonium sulfate, dialyzed and fractionated by size exclusion chromatography on Superdex G75. Fractions which eluted earlier than Nedd8 were pooled and concentrated by ultrafiltration to 15mg/ml and is designated here as FI. Proteins retained by the O-Sepharose were eluted by inclusion of 0.6 M NaCl in the equilibration buffer. The collected proteins were precipitated with 90% ammonium sulfate and dialyzed against 25 mM Hepes, pH7.5, and 1 mM DTT and concentrated to 15 mg/ml of protein. This fraction is designated here as FII. Fraction II was generated by collecting proteins that were retained by an anion-exchange gel (Q-Sepharose) while FI was obtained by further fractionation of unretained proteins by gel filtration. Incubation of $^{125}$I-Nedd8 with FII, but not with FI, produced a radiolabeled band on SDS-gel which migrated at 59 kDa. Formation of this radiolabeled species required the presence of ATP, and this species could not be detected when DTT was included in the SDS-gel sample buffer. Thus, FII contains an activity which attaches Nedd8 to a protein via a DTT-sensitive linkage. Incubation of $^{125}$I-Nedd8 with FI and FII together resulted in the formation of two additional radiolabeled bands on SDS-gel, migrating at 30 and 97 kDa. Only the 30 kDa species exhibited DTT sensitivity. One interpretation of this result is the presence of a Nedd8-conjugating enzyme in FI which serves to accept Nedd8 from its activating enzyme in FII to form a 30 kDa thioester.

EXAMPLE 3

Purification of NEDD8-Activating Enzyme

To purify the protein in FII which forms the DTT-sensitive linkage to Nedd8, we immobilized Nedd8 to CH-Sepharose 4B gels and used DTT to elute protein that were initially retained by the gel matrix, as follows. Nedd8-affinity gel was prepared by coupling purified Nedd8 to activated CH Sepharose 4B (Pharmacia) according to manufacturer's instructions and lead to the coupling of 5 mg of Nedd8/ml of gel beads. 100 mg of FII protein in a 9 ml reaction buffer containing MgATP and an ATP regenerating system was applied to 1 ml of Nedd8-immobilized gel beads at room temperature. The column was washed sequentially with 5 bed volumes of buffer A (50 mM Tris-HCl buffer, pH 7.5), buffer A with 0.5M NaCl, and buffer A. A buffer containing 50 mM Tris-HCl, pH 9.0 and 10 mM DTT was used to elute bound proteins. Analysis of the eluted proteins by SDS-PAGE and silver-staining revealed the presence of two major proteins that migrated at 60 and 49 kDa. A third major protein, migrating at 43 kDa, eluted as a broad peak. When the eluted proteins were analyzed by gel filtration chromatography, the 43 kDa protein eluted as a large aggregate at the void volume while p60 and p49 were found to co-elute with a retention time similar to that of the 110 kDa ubiquitin-activating enzyme, suggesting that these two proteins form a heterodimer. To determine which one of these two proteins forms the DTT-sensitive linkage with Nedd8, proteins purified from the Nedd8-affinity chromatography step were tested. The result is consistent with p49 being the Nedd8 acceptor. This protein is quantitatively absent only when ATP or AMPPNP was included in the reaction and only if the electrophoresis was carried out in the absence of DTT. The fact that no new discrete protein band was detected under conditions in which p49 was absent is likely due to the presence of p60 which precludes the detection of proteins that would migrate with similar mobility. In a separate experiment, the use of $^{125}$I-Nedd8 in the reaction led to the detection of a DTT-sensitive 59 kDa band, confirming the presence of a Nedd8-containing thioester. The ability of AMPPNP to substitute for ATP suggests that NEDD8 activation, similar to ubiquitin and SUMO-1, involves the intermediate formation of an enzyme-bound Nedd8-adenylate prior to thioester linkage.

EXAMPLE 4

Sequence Determination of NEDD8-Activating Enzyme

To obtain the identity of p49, this protein was excised from an SDS-gel, digested with trypsin and peptides were eluted and purified by HPLC as follows. The peak fractions form Nedd8-affinity chromatography step were concentrated and separated by SDS-PAGE, stained with Coomassie Brilliant Blue, and bands corresponding to p49 and p60 were excised. The gel slices were digested with trypsin, peptides were extracted and purified by microbore reversed-phase HPLC (PE-Applied Biosystems model 140A/1000S system) on Zorbax SB-C18 silica columns (1×150 mm). using linear gradients of acetonitrile in 0.08% aqueous trifluoroacetic acid (TFA), essentially as described in (J. Pohl et al, FEBS Lett. 272, 200, 1990.). The masses of the peptides were determined by matrix-assisted laser desorption ionization mass spectrometry (MALDI-TOF) using a Bruker Instruments model ProFlex MALDI-TOF instrument operated in the reflection mode; 2,5-dihydroxybenzoic acid was used as the sample matrix. The sequences of the peptides were determined by automated Edman degradation on a PE-Applied Biosystems model Procise HT sequencer system operated in the pulsed-liquid mode using manufacturer's supplied sequencing cycles. Two tryptic peptide sequences are determined (shown as underlined in FIG. 1), and these sequences were used to search the protein as well as the expressed sequence tag (EST) data bases. Although these sequences did not match known proteins in the data bases, two groups of EST clones could be identified whose translated amino acid sequence yielded perfect matches to either one of the two tryptic peptides. Further homology search with these EST sequences identified additional EST clones with overlapping sequences. Analysis of these EST clones enabled us to obtain a contiguous open reading frame (ORF) that encodes a 442-residue protein which contains the two tryptic peptide sequences. The nucleotide sequence of this ORF was confirmed by direct nucleotide sequencing of two EST clones (AA40862 and R57021). Analysis of this protein sequence revealed three regions of homology with human Uba1. Region I contains the putative ATP binding site found in Uba1 which is also present in yeast Uba2, and region II contains the PXCT sequence motif found in Uba1 in which the cysteine residue was identified by mutational analysis to form thiolester linkage with ubiquitin. These similarities are expected if the activation of Nedd8 utilizes a mechanism similar to that of ubiquitin and Smt3. Since p49 forms a heterodimer with p60 and functions as a protein component of Nedd8 activation, we designate it as Nae$_{-beta}$ and p60 as Nae$_{-alpha}$ Searches of the data banks with this protein sequence identified an open reading frame in S. pombe, and one in C. elegan which code for similar size proteins. In addition, a S. cerevisiae 299-residue protein, despite its smaller size, also shows extensive homology with this human protein. These are likely homologues of Nae$_{-beta}$ in different species since identical and highly conserved residues among these four proteins are interspersed throughout most of the protein whereas their homology to Uba1 and Uba2 is limited to defined regions only.

EXAMPLE 5

Identification of Nae-alpha

The similarity between Nedd8- and Smt3-activating enzyme in their subunit structure suggested that p60 or Nae$_{-alpha}$ would also contain a sequence stretch that shares homology to the N-terminal portion of Uba1. Using procedures similar to those with p49, three tryptic peptide sequences (SEQ ID NOS.: 26–28) were obtained for p60. These sequences FTVVATQLPEXTXL, EHFQSYDLDHME, and QTPSFWILA yielded perfect matches to residues 123–138, 194–205 and 300–308 in the 534-residue APP-BP1. In addition mass spectrometry of 15 of the tryptic peptides revealed matches within 1 Da of the expected mass of tryptic peptides of APP-BP1. These matches covered 37% of the APP-BP1 sequence. Thus, we concluded that Nae$_{-alpha}$ is indeed APP-BP1.

EXAMPLE 6

Identification and Cloning of NCE1

The putative human homology of yeast Ubc12 was identified by searching the human EST database for clones having coding sequences that are homologous to the yeast protein. An initial search using the yeast protein sequence identified several clones. Clone AA261836, which contains a coding sequence very similar to a region of the yeast protein was used to search for further EST clones. The search led to the construction of a contiguous consensus sequence from overlapping clones which predicts a gene to encode a protein having 183 amino acids, with a predicted molecular mass of 20899 Da. The contiguous nucleotide sequence was obtained using nested PCR on a human leukocyte cDNA library. The first PCR used primers having the sequences (SEQ ID NOS.: 29 and 30) GCAGGATGAT-CAAGCTGTTCTCGC (forward) and CGTG-GCGGGGGTGGGTATGCGCCA (reversed). The second PCR used the primers (SEQ ID NOS.: 31 and 32) CGG-GAATTCCATATGATCAAGCTGTTCTCGCTG (forward) and CGCCCAAGCTTCTATTTCAGGCAGCGCTCAAAG (reversed). The PCR product was digested with Nde1 and HindIII and ligated with similarly digested plasmid pT7-7. The resulting clone, pT7-7-UbcH12, was sequenced to determine the nucleotide sequence (SEQ ID NO 3) and deduced amino acid sequence (SEQ ID NO 4) shown in FIG. 1. FIG. 2 shows the alignment of NCE1 with yeast Ubc12. NCE1 shows 41% identity and 63% homology with yeast Ubc12.

EXAMPLE 7

Expression and Purification of NCE1

BL21 (DE3) bacterial cells (Nowagen, Madison, Wis.; catalog no. 69450-1) were transformed with pT7-7-UbcH12 plasmid using conventional procedures. The transformed bacteria were induced to express the NCE1 protein by adding, to a final concentration of 1 mM, isopropyl-b-D-thiogalactopyranoside (IPTG) to an exponentially growing culture. The culture was allowed to grow for an additional 3 hours at 37° C. NCE1 protein was purified from lysed cells by sequential anion exchange and size exclusion chromatography. For anion exchange chromatography, the bacterial extract was loaded at a protein/gel ratio of 15 mg protein/ml gel onto Q-Sepharose (Pharmacia, Piscataway, N.J.) equilibrated with 50 mM HEPES (pH 7.8) and 1 mM DTT. NCE1 protein was retained by the gel and eluted using a linear NaCl gradient in the gel equilibration buffer. Fractions containing NCE1 protein were determined by assaying for NEDD8 thioester formation. NCE1 was found to elute at 0.08 M NaCl. Active fractions were pooled and concentrated by microfiltration and then subjected to size exclusion chromatography on Superdex-75 (Pharmacia) using a column buffer of 50 mM HEPES (pH 7.8), 1 mM DTT and 50 mM NaCl. Fractions were assayed for NEDD8-thioester formation. NCE1 eluted at a volume expected for a 19 kDa protein, suggesting that it exists as a monomer. SDS-PAGE analysis with Coomassie stain indicated that the preparation was predominantly (>90%) NCE1 protein. Purified NCE1 protein migrated on an 8% TRICINE gel at a molecular weight of 21 kDa (data not shown). Extending the N-terminus of NCE1 with the amino acid sequence (SEQ ID NO.: 33) MHHHHHH resulted in an NCE1 variant protein that retained activity in NEDD8-thioester formation. The six histidine residues provide a nickel binding site and allowed this variant to be purified with Ni-NTA or other metal affinity chromatography procedures.

EXAMPLE 8

Thioester Formation Between NCE1 and NEDD8

Proteins (as indicated below) were incubated in a reaction buffer containing 25 mM Hepes (pH7.0), 10 mM $Mg^{2+}$ and 1 mM ATP for 5 minutes at 30° C. The reaction was stopped by addition of SDS sample loading buffer. Each sample was divided into two aliquots, to one of which was added DTT to a final concentration of 10 mM. The DTT-containing sample was heated in a 95° C. bath for two minutes. Samples were separated on 10% SDS-Tricine PAGE, followed by silver staining. The results are shown in FIG. 4. Lanes 1–4 are reaction mixtures 1–4. Lanes 5–8 are reaction mixtures 1–4 which were incubated with 10 mM DTT and heated to 90° C. for two minutes prior to electrophoresis. These results show that NCE1 migrates at a slower rate in the presence of NEDD8 and Nae, and that this is reversible by DTT. Ubiquitin activating enzyme, E1, cannot substitute for NAE in providing this result. These data support the view that NCE1 is a NEDD8 conjugating enzyme which forms a thioester with NEDD8 in the presence of activating enzyme, NAE.

| Reaction No. | Proteins |
|---|---|
| 1 | NAE + NEDD8 |
| 2 | NCE1 + NEDD8 |
| 3 | NCE1 + NEDD8 + NAE |
| 4 | NCE1 + NEDD8 + ubiquitin activating enzyme, E1 |

EXAMPLE 9

Identification and Cloning of NCE2

The human EST database was searched using a query sequence (SEQ ID NO.: 34) HPNITETICLSLLREHSIDGT-GWA. This is the sequence of clone AA306113 and bears similarity to the active site of proteins in the UBC protein family. Clones were identified which had sequences overlapping the sequence of clone AA306113. The identified sequences of the overlapping EST clones were aligned by the program CLUSTALW (See Thompson et al., Nucleic Acids Res. 22: 4673–4680 (1994), or by the program SeqMan (DNASTAR, Inc., Madison, Wis.) to yield a consensus sequence, CON1. CON 1 was used to perform searches for additional clones with overlapping sequences. The overlapping sequences yielded an open reading frame which encodes a protein of 185 amino acids (predicted molecular mass=21076 Da). Based upon homology to known human Ubc proteins, this gene is a member of the human Ubc gene family. The contiguous nucleotide sequence of NCE2 was obtained using nested PCR on a human leukocyte cDNA library. The first PCR used the primers (SEQ ID NOS.: 35 and 36) AGCCCAGGG-TAAAGGCAGCA (forward) and CATGTTAGAGA-CAAACTGTA (reversed). The second PCR used the primers (SEQ ID NOS.: 37 and 38) GGGAATTCCATATGCTAACGCTAGCAAGTAA (forward) and CCATCGATTCATCTGGCATAACGTTTGA (reversed). The PCR product was then cloned into the NdeI/HindIII sites of pT7-7 to generate the plasmid pt7-7-HSUBC17. The sequence of the NCE2 gene and its deduced amino acid sequence are shown in FIG. 4. No close homolog exists in the yeast genome. The protein has 46% identity and 64% homology with a *C. elegans* gene (Genebank Accession #CE 275850) of unknown function (see FIG. 5).

EXAMPLE 10

Expression and Purification of NCE2

BL21 (DE3) bacterial cells were transformed with pT7-7-UbcH17 plasmid using conventional procedures. The transformed bacteria were induced to express the NCE2 protein by adding, to a final concentration of 1 mM, isopropyl-b-D-thiogalactopyranoside (IPTG) to an exponentially growing culture. The culture was allowed to grow for an additional 3 hours at 37° C. NCE2 protein was purified from lysed cells by sequential anion exchange and size exclusion chromatography. For anion exchange chromatography, the bacterial extract was loaded at a protein/gel ratio of 15 mg protein/ml gel onto Q-Sepharose (Pharmacia) equilibrated with 50 mM HEPES (pH 7.8) and 1 mM DTT. NCE2 protein was retained by the gel and eluted using a linear NaCl gradient in the gel equilibration buffer. Fractions containing NCE2 protein were determined by assaying for NEDD8 thioester formation. NCE2 was found to eluate at 0.8 M NaCl. Active fractions were pooled and concentrated by microfiltration and then subjected to size exclusion chromatography on Superdex-75 (Pharmacia) using a column buffer of 50 mM HEPES (pH 7.8), 1 mM DTT and 50 mM NaCl. Fractions were assayed for $^{125}$I-NEDD8-thioester formation. NCE2 eluted at a volume expected for a 21 kDa protein, suggesting that it exists as a monomer. SDS-PAGE analysis with Coomassie stain indicated that the preparation was predominantly (>90%) NCE2 protein. Purified NCE2 protein migrated on an 8% TRICINE gel at a molecular weight of 21 kDa (data not shown).

EXAMPLE 11

Thioester Formation Between NCE2 and NEDD8

The ability of NCE2 to form a thioester bond with NEDD8 was assessed as follows. NCE2 protein, either purified or from bacterial lysate, was incubated with $^{125}$I-NEDD8 ($10^6$ cpm/μg) in a buffer containing 25 mM HEPES (pH 7.0), 10 mM $MgCl_2$, 1 mM ATP and 20 nM purified NAE1 or ubiquitin-activating enzyme. The reaction was allowed to proceed at 30° C. for 5 minutes. The reaction was stopped by adding SDS-sample buffer either with or without 10 mM DTT. The samples were subjected to SDS-PAGE and autoradiography. In the reaction containing NCE2 (lane 3), the autoradiograph showed two radiolabelled bands with apparent molecular masses of 7 and 29 kDa, which are the expected molecular masses of NEDD8 and NEDD8-NCE2, respectively. Only the 7 kDa band was detected when the sample was incubated in 10 mM DTT prior to electrophoresis, consistent with the 29 kDa band being a NEDD8-NCE2 thioester. Analogous reactions containing NCE1 in place of NCE2 (lanes 2 and 4) are shown for comparison. These results demonstrate that NCE2 is capable of forming a thioester bond with NEDD8, but not with ubiquitin, in a NAE-dependent reaction. These data support the view that NCE2 is a NEDD8 conjugating enzyme.

EXAMPLE 12

Preparation of Dominant Negative Mutants

The active site cysteine of a cloned NCE1 or NCE2 is assigned by examining the sequence alignment with known Ubc proteins (see FIG. 6 for alignment). The active site cysteine is replaced by a serine using standard site-specific mutagenesis. The mutant protein is expressed in bacteria and purified. The ability of the mutant protein to form a stable oxygen ester with NEDD8 is established as described in Examples 8 and 11 above, except that the bond formation is not liable in DTT. Dominant negative mutant activity is then established by introducing the mutant protein in increasing concentrations in an assay as described in Examples 8 and 11 above and demonstrating dose-dependent inhibition of NEDD8/NCE1 or NCE2 complex formation.

What is claimed is:

1. A purified NEDD8-activating protein beta subunit (NAE1-beta), comprising an amino acid sequence set forth in SEQ ID NO: 2, wherein the subunit has the activity of forming a thioester linkage with NEDD8.

2. An NAE1-beta expression element that is an isolated or recombinant nucleic acid sequence encoding NAE1-beta comprising of SEQ ID NO: 2 and having NAE1-beta biological activity comprising forming a thioester linkage with NEDD8.

3. A method for identifying NAE1BBMs comprising contacting purified NAE1-beta according to claim 1 with populations of molecules or mixed populations of molecules and determining the presence of molecules which bind specifically to NAE1-beta.

4. A method for determining the presence or absence and/or quantity of NAE1-beta nucleic acid in a biological sample comprising: a) hybridizing a nucleic acid sequence which is specifically complementary to SEQ ID NO: 1 to a biological sample, thereby forming a hybridization complex; and b) detecting said hybridization complex, wherein the presence of said hybridization complex indicates the presence of NAE-1 beta nucleic acid.

5. An NAE1-beta expression element that is an isolated or recombinant nucleic acid sequence comprising the nucleic acid sequence set forth in SEQ ID NO: 1, wherein the expression element has NAE1-beta biological activity comprising forming a thioester linkage with NEDD8.

6. An NAE1-beta expression element that is an isolated or recombinant nucleic acid sequence encoding NAE1-beta comprising of SEQ ID NO: 2 with the cysteine residue at position 216 replaced with serine and having activity as a dominant negative mutant thereof, wherein the dominant negative mutant inhibits the ability of NAE1 to form a thioester linkage with NEDD8 or to transfer NEDD8 to a NEDD8 conjugating enzyme.

7. An NAE1-beta expression element that is a vector or recombinant expression unit comprising the nucleic acid sequence of claim 5.

8. An NAE1-beta expression element that is a vector recombinant expression unit comprising the nucleic acid sequence of claim 2 or 6.

* * * * *